United States Patent [19]
Sebti et al.

[11] Patent Number: 5,834,434
[45] Date of Patent: *Nov. 10, 1998

[54] INHIBITORS OF FARNESYLTRANSFERASE

[75] Inventors: Said M. Sebti; Andrew Hamilton, both of Pittsburgh, Pa.

[73] Assignee: University of Pittsburgh, Pittsburgh, Pa.

[ * ] Notice: The term of this patent shall not extend beyond the expiration date of Pat. No. 5,602,098.

[21] Appl. No.: 451,839

[22] Filed: May 30, 1995

Related U.S. Application Data

[63] Continuation-in-part of Ser. No. 62,287, May 18, 1993, Pat. No. 5,602,098.

[51] Int. Cl.$^6$ .................................................. A61K 38/05
[52] U.S. Cl. ........................... 514/19; 562/545; 562/557; 562/559
[58] Field of Search .............................. 514/19; 562/557, 562/559, 445

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham et al. | 514/18 |

FOREIGN PATENT DOCUMENTS

| | | | |
|---|---|---|---|
| 2072033 | 6/1992 | Canada . | |
| 0203587 | 12/1986 | European Pat. Off. . | |
| 0456180 | 11/1991 | European Pat. Off. . | |
| 0461869 | 12/1991 | European Pat. Off. . | |
| 0512865 | 11/1992 | European Pat. Off. . | |
| 0520823 | 12/1992 | European Pat. Off. . | |
| 0523873 | 1/1993 | European Pat. Off. . | |
| 0528486 | 2/1993 | European Pat. Off. | C07K 5/10 |
| 0534546 | 3/1993 | European Pat. Off. | C07F 9/38 |
| 0535730 | 4/1993 | European Pat. Off. | C07K 5/08 |
| WO116340 | 10/1991 | WIPO . | |
| WO9116340 | 10/1991 | WIPO . | |
| WO9218465 | 10/1992 | WIPO . | |
| WO9409766 | 5/1994 | WIPO . | |

OTHER PUBLICATIONS

Hancock et al, "A polybasic Doamin or Palmitoylation is Required in Addition to the CAAX Motif to Localize p21$^{ras}$ to the Plasma Membrane", Cell. vol. 63, Oct. 5, 1990. pp. 133–139.

Reiss et al, "Inhibition of Purified p21$^{ras}$ Farnesyl:Protein Transferase by Cyc–AAX Tetrapeptides", Cell, vol. 62, Jul. 13, 1990, pp. 81–88.

Willumsen et al, "The p21 ras C–terminus is required for transformation and membrane association," Nature, vol. 310, Aug. 16, 1984, pp. 583–586.

Gibbs, J.B., Ras C–Terminal Processing Enzymes–New Drug Targets, Cell, 65:1–4 (1991).

Gibbs et al., Farnesyltransferase Inhibitors: Ras Research Yields a Potential Cancer Terapeutic, Cell, 77:175–178 (1994).

Brown et al., Tetrapeptide inhibitors of protein farnesyltransferase: Amino–terminal substitution in phenylalanine–containing tetrapeptides restores farnesylation, Proc. Natl. Acad. Sci. U.S.A., 89:8313–8316 (1992).

Kohl et al., Selective Inhibition of ras–Dependent Transformation by a Farnesyltransferase Inhibitor, Science, 260:1934–1937 (1993).

Graham et al., Pseudopeptide Inhibitors of Ras Farnesyl–Protein Transferase, J. Med. Chem.,37:725–732 (1994).

Garcia et al., Peptidomimetic Inhibitors of Ras Farnesylation and Function in Whole Cells, J. Biol. Chem., 268:18415–18418 (1993).

Nigam et al., Potent Inhibition of Human Tumor p21$^{ras}$ Farnesyltransferase by $A_1A_2$–lacking p21$^{ras}$ $CA_1A_2X$ Peptidomimetics, J. Biol. Chem., 268:20695–20698 (1993).

Qian et al., Design and Structural Requirements of Potent Peptidomimetic Inhibitors of p21$^{ras}$ Farnesyltransferase, J. Biol. Chem. 269:12410–12413 (1994).

Qian et al., Peptidomimetic Inhibitors of P21RAS Farnesyltransferase: Hydrophobic Functionalization Leads to Disruption of P21RAS Membrane Association in Whole Cells, Bioorg. Med. Chem. Lett., 4:2579–2584 (1994).

Goldstein et al., Benzodiazepine Peptidomimetics: Potent Inhibitors of Ras Farnesylation in Animal Cells, Science, 260:1937–1942 (1993).

Reiss et al., Inhibition of Purified p21$^{ras}$ Farnesyl:Protein Transferase by Cys–AAX Tetrapeptides, Cell, 62:81–88 (1990).

Vogt et al., A Non–peptide Mimetic of Ras–CAAX:Selective Inhibition of Farnesyltransferase and Ras Processing, (1995) J. Biol. Chem. 270:660–664.

Kohl et al., Protein farnesyltransferase inhibitors block the growth of ras–dependent tumors in nude mice, (1994) Proc. Natl. Acad.Sci. USA 91:9141–9145.

Cox et al., The CAAX Peptidomimetic Compound B581 Specifically Blocks Farnesylated, but Not Geranylgeranylated or Mynistylated, Oncogenic Ras Signaling and Transformation, (1994) J. Biol. Chem. 269:19203–19206.

Hancock et al, "A polybsic Domain or Palmitoylation is Required in Addition to the CAAX Motif to Localize p21$^{ras}$ in the Plasma Membrane", Cell. vol. 63. Oct. 5, 1990, pp. 133–139.

Reiss et al., "Inhibition of Purified p21$^{ras}$ Farnesyl:Protein Transferase by Cys–AAX Tetrapeptides", Cell, vol. 62, Jul. 13, 1990. pp. 81–88.

Willumsen et al. "The p21 ras C–terminus is required for transformation and membrane association," Nature, vol. 310. Aug. 16, 1984, pp. 583–586.

*Primary Examiner*—Cecilia J. Tsang
*Assistant Examiner*—David Lukton
*Attorney, Agent, or Firm*—Cushman Darby & Cushman IP Group of Pillsbury Madison & Sutro LLP

[57] ABSTRACT

Peptidomimetics of the formula CβX where C is cysteine, X is any naturally occuring amino acid, and β is a hydrophobic spacer, most notably 2-phenyl-4-aminobenzoic acid. These compounds are effective inhibitors of p2lras farnesyltrasferase, block Ras-dependent oncogenic signalling and inhibit human tumor growth in vivo in animal models. Pro-drugs made by functionalizing terminal amino and carboxylic acid groups of peptides and peptidomimetics are also disclosed. Such functionalized derivatives demonstrate increased cell uptake. Other structural modifications are also disclosed.

17 Claims, 11 Drawing Sheets

CVIM

FTI-249

FTI-276: R = O⁻
FTI-277: R = OCH₃ log M FTI-276

RAS

INHIBITORS OF FARNESYLTRANSFERASE

This patent application is a continuation-in-part of 08/062,287, filed May 18, 1993, now U.S. Pat. No. 5,602, 098. The invention was supported by grants from the American Cancer Society and the National Cancer Institute (NIH). The government has certain rights in the invention.

INTRODUCTION

The present invention relates to novel peptidomimetics and other compounds which are useful as inhibitors of p21ras farnesyltransferase and as anti-cancer drugs. Farnesylation is required for the cancer causing activity of the oncogene product p21ras. Hence there is considerable interest in inhibiting farnesylation.

BACKGROUND OF THE INVENTION

Ras proteins are plasma membrane-associated GTPases that function as relay switches that transduce biological information from extracellular signals to the nucleus (29–31). In normal cells Ras proteins cycle between the GDP-(inactive) and GTP-(active) bound forms to regulate proliferation and differentiation. The mechanism by which extracellular signals, such as epidermal and platelet derived growth factor (EGF and PDGF), transduce their biological information to the nucleus via Ras proteins has recently been unraveled (29–31). Binding of the growth factors to tyrosine kinase receptors results in autophosphorylation of various tyrosines which then bind src-homology 2 (SH2) domains of several signaling proteins. One of these, a cytosolic complex of GRB-2 and a ras exchanger (m-SOS-1), is recruited by the tyrosine phosphorylated receptor where mSOS-1 catalyzes the exchange of GDP for GTP on Ras, hence activating it. GTP-bound Ras recruits Raf, a serine/threonine kinase, to the plasma membrane where it is activated. Raf triggers a kinase cascade by phosphorylating mitogen-activated protein (MAP) kinase/extracellular-regulated protein kinase (ERK) kinase (MEK) which in turn phosphorylates MAP Kinase on threonine and tyrosine residues. Activated MAP Kinase translocates to the nucleus where it phosphorylates transcription factors (31). Termination of this growth signal is accomplished by hydrolysis of Ras-GTP to Ras-GDP.

Ras oncogenes are the most frequently identified activated oncogenes in human tumors (1–3). In a large number of human cancers, Ras is GTP-locked because of mutations in amino acids 12, 13, or 61 and the above Ras pathway no longer requires an upstream growth signal and is uninterrupted. As a consequence, enzymes in this pathway such as Raf, MEK and MAP Kinase are constitutively activated.

In addition to its inability to hydrolyze GTP, oncogenic Ras must be plasma membrane-bound to cause malignant transformation (13). Ras is posttranslationally modified by a lipid group, farnesyl, which mediates its association with the plasma membrane (10–14).

Post-translational events leading to membrane association of p21ras have previously been disclosed (10–14). The p21ras proteins are first made as pro-p21ras in the cytosol where they are modified on cysteine 186 of their carboxyl terminal sequence $CA_1A_2X$ (C =cysteine, $A_1$ and $A_2$ =isoleucine, leucine or valine and X =methionine or serine) by the cholesterol biosynthesis intermediate farnesyl pyrophosphate (FPP). This farnesylation reaction is then followed by peptidase removal of the $A_1A_2X$ tripeptide and carboxymethylation of the remaining cysteine. The processed p21ras proteins associate with the inner surface of the plasma membrane and are further modified on cysteines 181–184 by another lipid, palmitic acid (10–14).

p21Ras farnesyltransferase, the enzyme responsible for catalyzing the transfer of farnesyl, a 15-carbon isoprenoid, from FPP to the cysteine of the $CA_1A_2X$ carboxyl terminus of p21ras, has been purified to homogeneity from rat brain (15,16). The enzyme is a heterodimer composed of α and β subunits of molecular weights 49 and 46 kDa, respectively (17). The β subunit has been shown to bind p21ras (17). Because p21ras farnesylation and subsequent membrane association are required for p21ras transforming activity (13), it has been proposed that p21ras farnesyltransferase would be a useful anticancer therapy target. Accordingly, an intensive search for inhibitors of the enzyme is underway (18–24, 33–44). Potential inhibitor candidates are $CA_1A_2X$ tetrapeptides which have been shown to be farnesylated by p21ras farnesyltransferase and appear to be potent inhibitors of this enzyme in vitro (15,18,21–24). Competition studies have demonstrated that $CA_1A_2X$ peptides with the greatest inhibitory activity are those where $A_1$ and $A_2$ are hydrophobic peptides with charged or hydrophilic residues in the central positions demonstrating very little inhibitory activity (18, 21, 23). A major drawback with the use of peptides as therapeutic agents is their low cellular uptake and their rapid inactivation by proteases.

The research efforts directed towards farnesyltransferase and the inhibition of its activity are further illustrated by the following patents or published patent applications:

U.S. Pat. No. 5,141,851
WO 91/16340
WO 92/18465
EPA 0456180 A1
EPA 0461869 A2
EPA 0512865 A2
EPA 0520823 A2
EPA 0523873 A1

Of the above disclosures, EPA 0520823 A2 discloses compounds which are useful in the inhibition of farnesyl-protein transferase and the farnesylation of the oncogene protein ras. The compounds of EPA 0520823 A2 are illustrated by the formula:

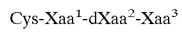

or pharmaceutically acceptable salts thereof,
wherein Cys is a cysteine amino acid;
$Xaa^1$ is an amino acid in natural L-isomer form;
dxaa2 is an amino acid in unnatural D-isomer form; and
$Xaa^3$ is an amino acid in natural L-isomer form.

The preferred compounds are said to be CV(Dl)S and CV(Df)M, the amino acids being identified by conventional 3 letter and single letter abbreviations as follows:

| Cysteine | Cys | C |
|---|---|---|
| Glycine | Gly | G |
| Isoleucine | Ile | I |
| Leucine | Leu | L |
| Lysine | Lys | K |
| Methionine | Met | M |
| Phenylalanine | Phe | F |
| Serine | Ser | S |
| Threonine | Thr | T |
| Valine | Val | V |

EPA 0523873 Al discloses a modification of the compounds of EPA 0520823 A2 wherein $Xaa^3$ is phenylalanine or p-fluorophenylalanine.

EPA 0461869 describes compounds which inhibit farnesylation of Ras protein of the formula:

Cys-Aaa¹-Aaa²-Xaa where $Aaa^2$ and $Aaa^2$ are aliphatic amino acids and Xaa is an amino acid. The aliphatic amino acids which are disclosed are Ala, Val, Leu and Ile. Preferred compounds are those where $Aaa^1$ is Val, $Aaa^2$ is Leu, Ile or Val and Xaa is Ser or Met.

Preferred specific compounds are:

Cys-Val-Leu-Ser

Cys-Val-Ile-Met

Cys-Val-Val-Met

U.S. Pat. No. 5,141,851 and WO 91/16340 disclose the purified farnesyl protein transferase and certain peptide inhibitors therefor, including, for example, CVIM, TKCVIM and KKSKTKCVIM.

WO 92/18465 discloses certain farnesyl compounds which inhibit the enzymatic methylation of proteins including ras proteins.

EPA 0456180 A1 is directed to a farnesylprotein transferase assay which can be used to identify substances that block farnesylation of ras oncogene gene products while EPA 0512865 A2 discloses certain cyclic compounds that are useful for lowering cholesterol and inhibiting farnesyl-protein transferase.

As will be evident from the foregoing, there is a great deal of research effort directed towards the development of inhibitors of farnesyltransferase. However, there still remains a need for improvements in this critically important area.

Although CAAX peptides are potent competitive inhibitors of FTase, rapid degradation and low cellular uptake limit their use as therapeutic agents. Our strategy to inhibit FTase has been to replace several amino acids in the CAAX motif by peptidemimics. The rationale behind this strategy is based on the existance of a hydrophobic pocket at the enzyme active site that interacts with the hydrophobic "AA" dipeptide of the carboxyl termini CAAX of Ras molecules. In the previous application (U.S. Ser. No. 08/062,287) we disclosed two very potent classes of inhibitors of FTase (i.e. Cys-3AMBA-Met and Cys-4ABA-Met). The peptidomimetic Cys-4ABA-Met incorporated a hydrophobic/aromatic spacer (i.e. 4-aminobenzoic acid) between Cys and Met. The present application discloses several derivatives of Cys-4ABA-Met where positions 2 and 3 of 4-amino benzoic acid were modified by several alkyl, and/or aromatic groups, compounds that show great promise of ability to selectively antagonize RAS- dependent signaling and to selectively inhibit the growth of human tumors with aberrant Ras function.

SUMMARY OF THE INVENTION

An important embodiment of the present invention is based on the finding that a novel group of peptidomimetics as represented by Formula (I) have a high inhibitory potency against human tumor p21ras farnesyltransferase and inhibit tumor growth of human carcinomas:

Cβx  (I)

where
C stands for the cysteine radical, or for the reduced form of the cysteine radical (R-2-amino-3- mercaptopropyl amine); β is the radical of a non-peptide aminoalkyl- or amino-substituted phenyl carboxylic acid; and X is the radical of an amino acid, preferably Met. Any other natural or synthetic amino acid can also be used at this position.

A particularly preferred compound of the invention is:

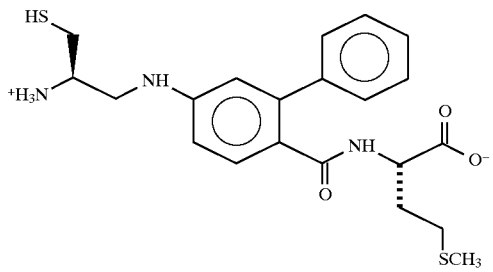

In this compound the cysteine radical is in the reduced form and the spacer group is 2-phenyl-4-aminobenzoic acid.

Another preferred form of the invention is:

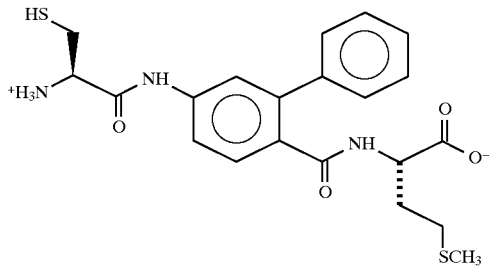

The compounds of Formula (I) are different from the prior art farnesyltransferase inhibitors in that they do not include separate peptide amino acids $A_1$, $A_2$ as in prior art inhibitors represented by the formula $CA_1A_2X$. The present compounds are consequently free from peptidic amide bonds.

It is also to be noted that the present compounds are not farnesylated by the enzyme. They are, therefore, true inhibitors, not just alternative substrates. This may explain the high inhibitory action of the present compounds relative to their parent compounds which are farnesylated.

A further important feature of the invention is the provision of the compounds of Formula (I) in the form of pro-drugs. Broadly speaking, this is accomplished by functionalizing the terminal end groups (amino, cysteine sulfur and carboxy groups) of the compounds with hydrophobic, esterase-sensitive moieties which serve to increase the plasma membrane permeability and cellular uptake of the compounds and consequently their efficiency in inhibiting tumor cell growth.

In this regard, a particularly preferred compound of the invention is the methylester form of FTI-276, which is illustrated in FIG. 1A. The above-mentioned pro-drug aspect of the invention is applicable not only to the compounds of the invention but also to prior peptide inhibitors $CA_1A_2X$ as well as any other peptide with potential for biological uses for the purpose of improving the overall effectiveness of such compounds, as hereinafter described.

Another important embodiment of the invention contemplates replacing the $A_1A_2X$ portion of the $CA_1A_2X$ tetrapeptide inhibitors with a non-amino acid component while retaining the desired farnesyltransferase inhibiting activity. These compounds may be illustrated by Formula (II):

CA  (II)

where C is cysteine and A represents an aryl or heterocyclic substituent such as 3-aminomethyl-biphenyl-3'-carboxylic acid, which does not include a peptide amino acid but corresponds essentially in size with $A_1A_2X$, as hereinafter described.

A further modification involves the provision of $CA_1A_2X$ tetrapeptides or CβX peptidomimetics which have been modified by functionalizing the sulfhydryl group of the cysteine C with an alkyl phosphonate substituent, as hereinafter described.

Other features of the invention will also be hereinafter apparent.

A. Structures of CVIM, FTI-249, FTI-276 and FTI- 277. FTI-276 and FTI-277were synthesized as described in Examples 10 and 11. B. FTase and GGTase I inhibition assays were carried out as described in Example 12 by determining the ability of FTI-276 to inhibit the transfer of farnesyl and geranylgeranyl to recombinant H-Ras-CVLS and H-Ras-CVLL, respectively. The data are representative of at least three different experiments.

Figure 2A:
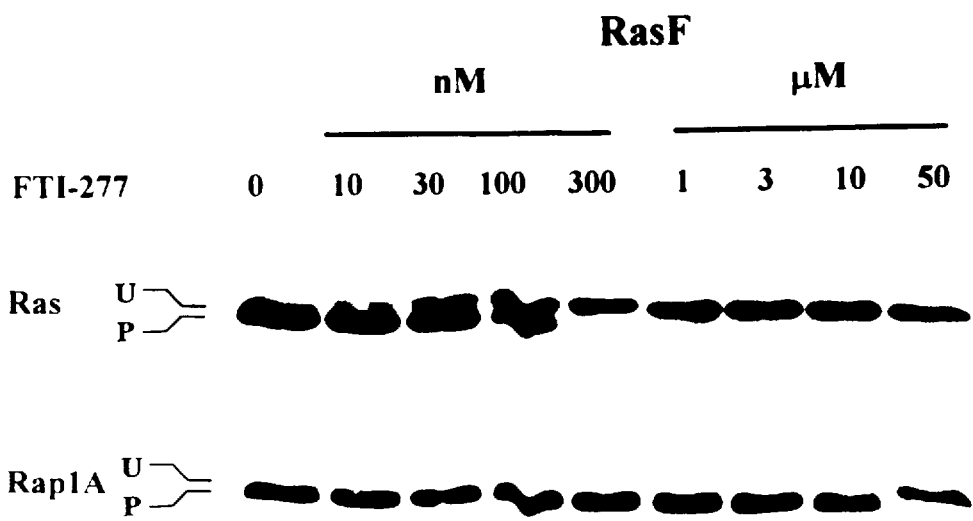
Figure 2B:
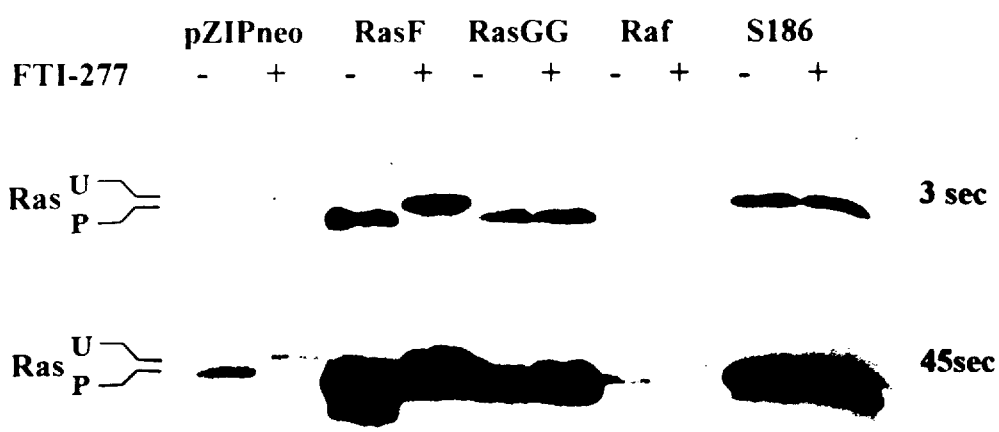

FIGS. 2A–2B: Inhibition of Ras and RaplA Processing

A. H-RasF cells were treated with various concentrations of FTI-277, lysed and the lysates immunoblotted with anti-Ras or anti-Rap1A antibodies as described in Example 13. B. pZIPneo, H-RasF, H-RasGG, Raf and S186 cells were treated with vehicle or FTI-277 (5 μM), lysed and lysates immunoblotted by anti-Ras antibody. Data is representative of 5 different experiments. The cells were obtained from Dr. Channing Der, University of North Carolina, Chapel Hill, North Carolina.

Figure 3:
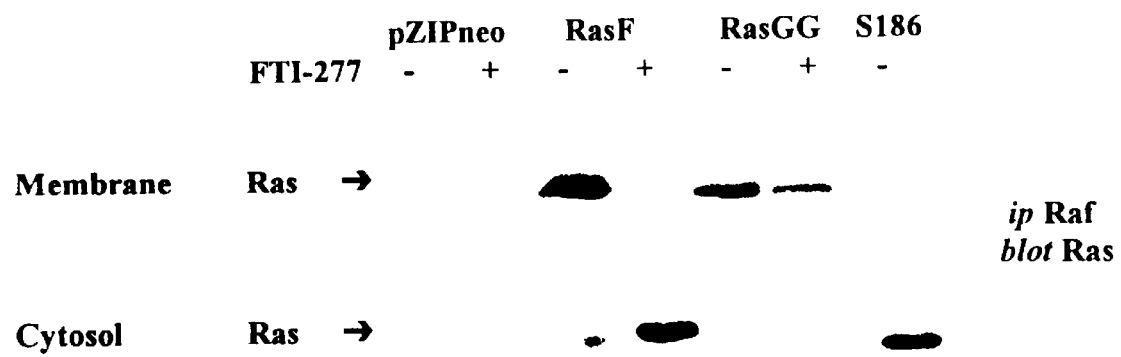

FIG. 3: Effects of FTI-277 on Ras/Raf Association.

pZIPneo, H-RasF, H-RasGG and S186 cells were treated with vehicle or FTI-277 (5 μM), homogenized and the membrane (A) and cytosolic (B) fractions were separated and immunoprecipitated by an anti-Raf antibody. The immunoprecipitates were then separated by SDS-PAGE and immunoblotted with anti-RAS antibody as described in Example 14. Data is representative of three different experiments.

Figure 4A:
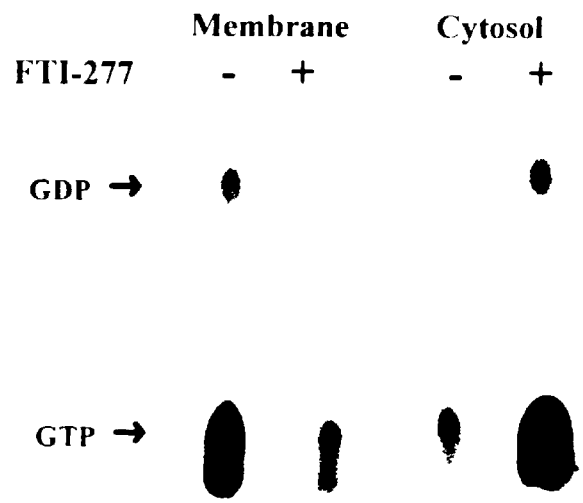
Figure 4B:
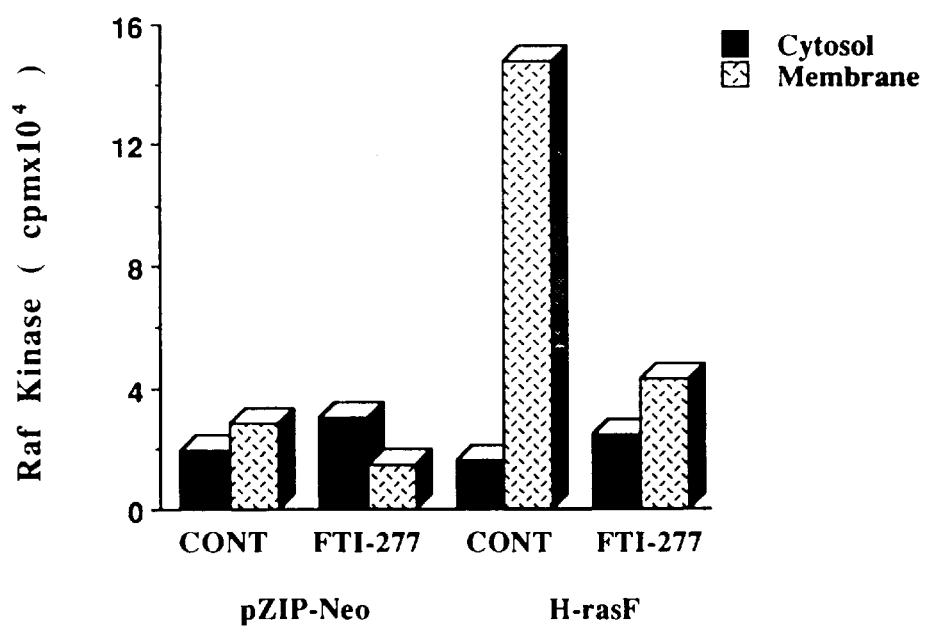

FIGS. 4A–4B: Effects of FTI-277 on Ras Nucleotide Binding and Raf Kinase Activity A: H-RasF cells were treated with vehicle or FTI- 277, lysed and the lysates immunoprecipitated with anti-Ras antibody. The GTP and GDP were then released from Ras and separated by TLC as described in Example 15. B: pZIPneo and H-RasF cells were treated with vehicle or FTI-277, lysed and cells lysates immunoprecipitated with an anti-Raf antibody. Raf kinase was assayed by using a 19-mer autophosphorylation peptide as substrate as described in Example 16. Data are representative of three different experiments.

Figure 5A:
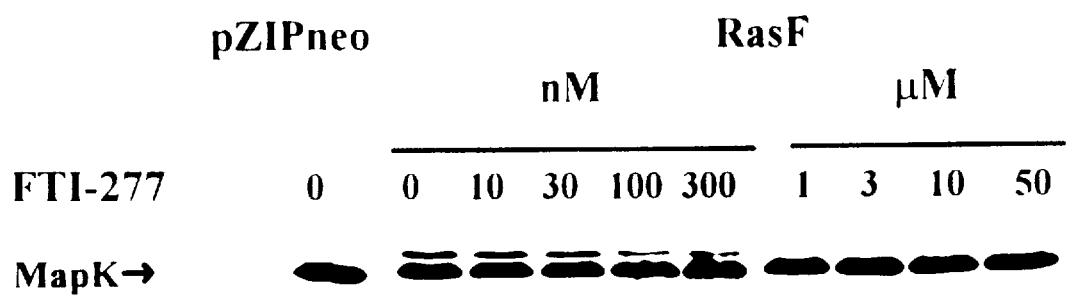
Figure 5B:
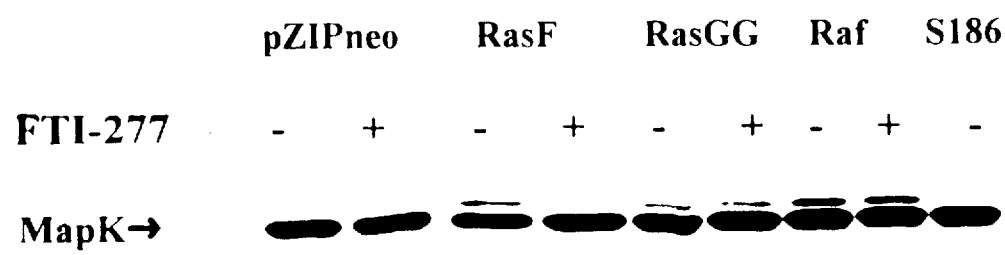

FIGS. 5A–5B: Effect of FTI-277 on Oncogenic Activation of MAPK

A: H-RasF cells were treated with various concentrations of FTI-277, cells lysed and lysates run on SDS-PAGE and immunoblotted with anti-MAPK antibody. B: pZIPneo, H-RasF, H-RasGG, Raf, and S186 cells were treated with vehicle of FTI-277 (5 μM), lysed and cells lysates processed as for A. Data are representative of two different experiments.

Figure 6:
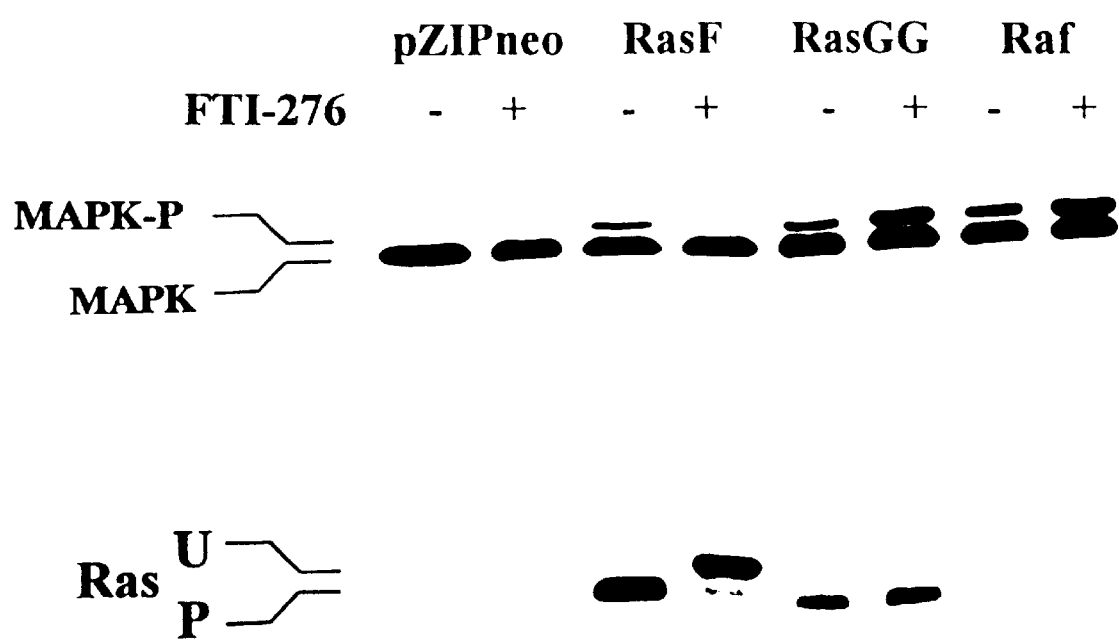

FIG. 6. FTI-276 inhibits selectively Ras processing and oncogenic Ras activation of MAP Kinase.

NIH 3T3 cells transfected with empty vector (pZIPneo), oncogenic (GTP-locked) farnesylated Ras (RasF), geranylgeranylated Ras (RasGG) or a transforming mutant of human Raf-1 were obtained from Channing Der and Adrienne Cox (University of North Carolina, Chapel Hill) (26, 27). The cells were plated in DMEM/10% CS (Dubelco's Modified Eagles Medium, 10% calf serum) on day one and treated with vehicle or FTI-270 (20 μM) on days 2 and 3. The cells were then harvested on day 4 and lysed in lysis buffer (30 mM HEPES, pH 7.51% TX-100, 10% glycerol, 10 mM NaCl, 5 mM $MgCl_2$, 25 mM NaF, 1 mM EGTA, 2 mM $Na_3VO_4$, 10 μg/ml Trypsin inhibitor, 25 μg/ml leupeptin, 10 μg/ml aprotinin, 2 mM PMSF). The lysate (35 μg) was electrophoresed on 15% SDS-PAGE, transferred to nitrocellulose membranes and immunoblotted simultaneously with anti-Ras antibody Y13-238 (isolated from hybridomas purchased from ATCC, Rockville, Md.) and an Anti-MAP kinase (erk2) antibody (UBI, Lake Placid, NY) as described previously (17, 22).

Figure 7A:
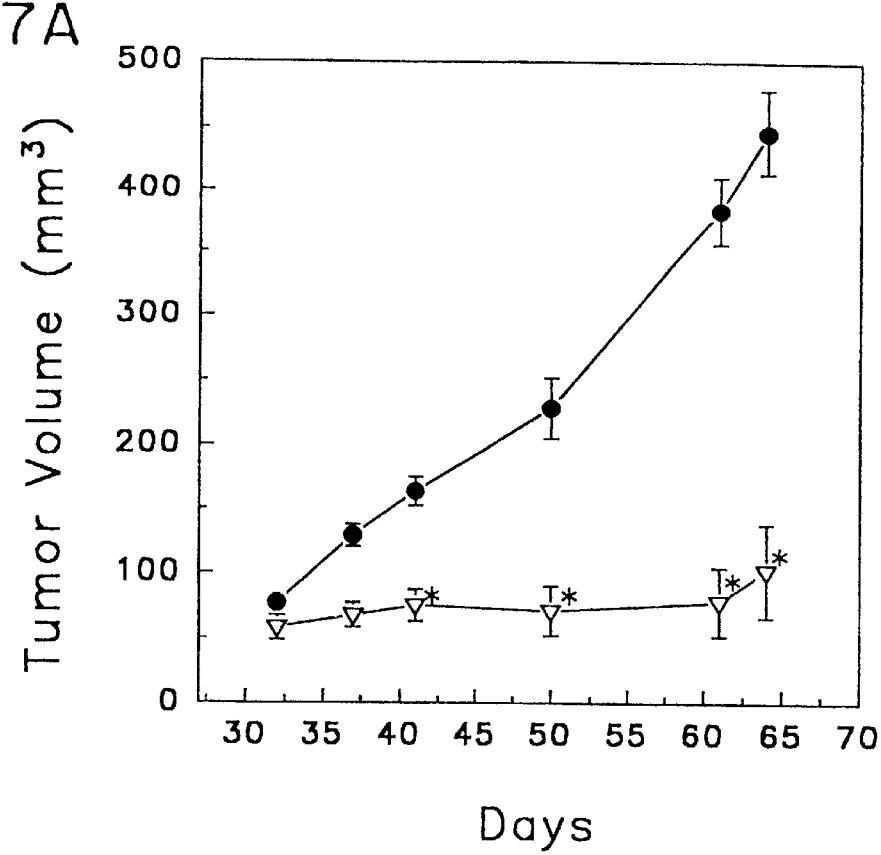
Figure 7B:
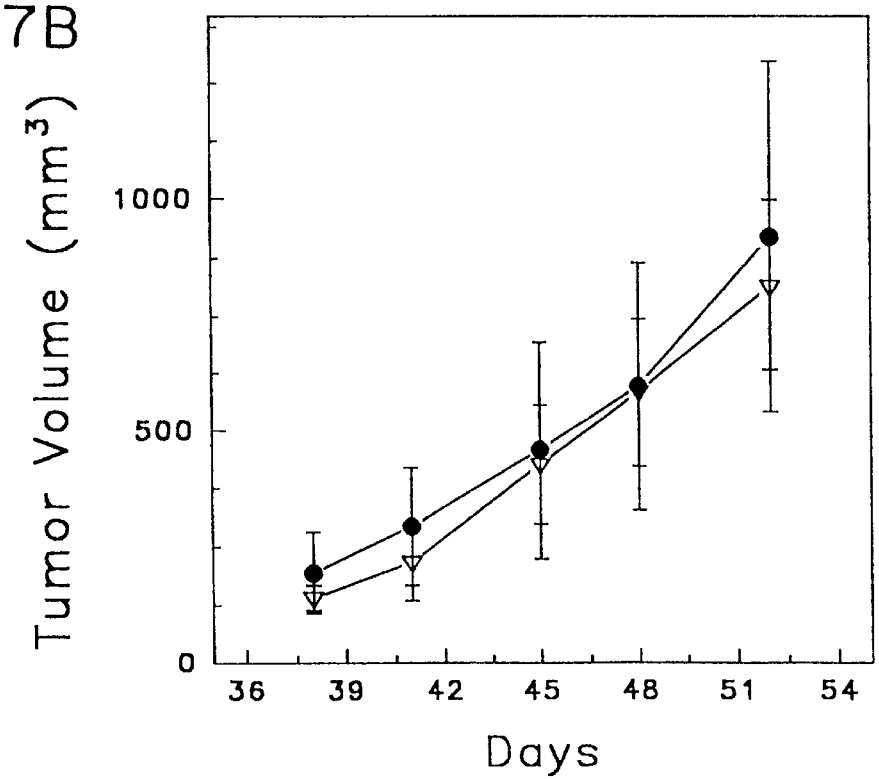

FIGS. 7A–7B. Antitumor efficacy of FTI-276 against human lung carcinomas.

Calu-1 (Panel A) and NCI- H810 cells (Panel B) were purchased from ATCC and grown in McCoy's 5A medium in 10% FBS (Fetal Bovine Serum) and RPMI 1640 in 10% FBS, respectively. The cells were harvested, resuspended in PBS and injected s.c. into the right and left flank of 8 week old female nude mice ($10^7$ cells/flank). Nude mice (Harlan Sprague Dawley, Indianapolis, Ind.) were maintained in accordance with the Institutional Animal Care and Use Committee (IACUC) procedures and guidelines. On day 32 after s.c. implantation of tumors, animals were dosed i.p. with 0.2 ml once daily for 36 days. Control animals (filled circles) received a saline vehicle whereas treated animals (open triangles) were injected with FTI-276 (50 mg/kg). The tumor volumes were determined by measuring the length (1) and the width (w) and calculating the volume (V =(1)×(w) $^2$/2). Data are presented as the average volume of eight tumors in each group for each cell line. Statistical significance between control and treated groups were evaluated by using student t test (*P<0.05).

Figure 8A:
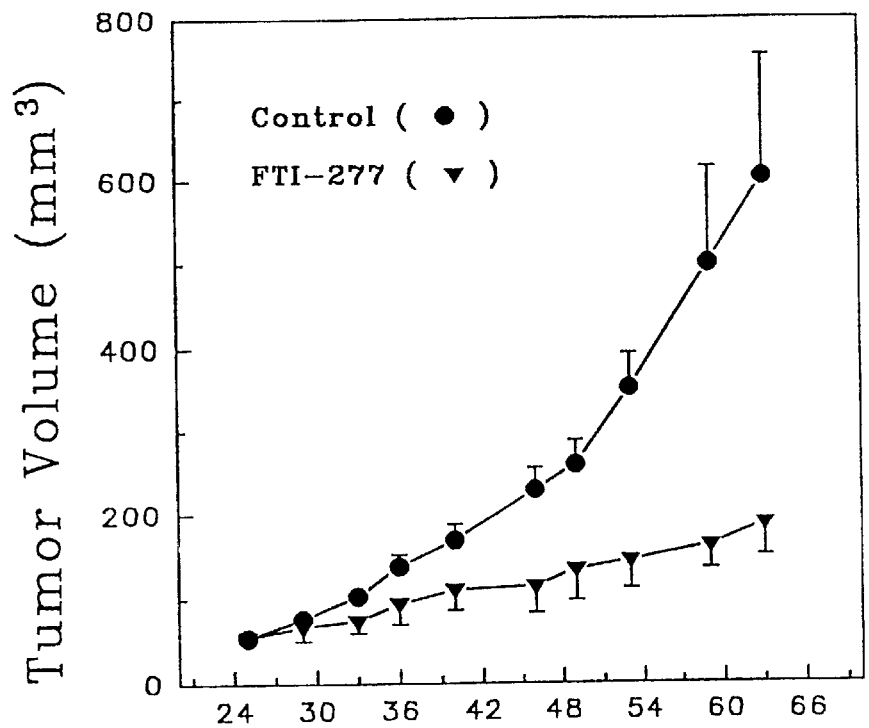
Figure 8B:
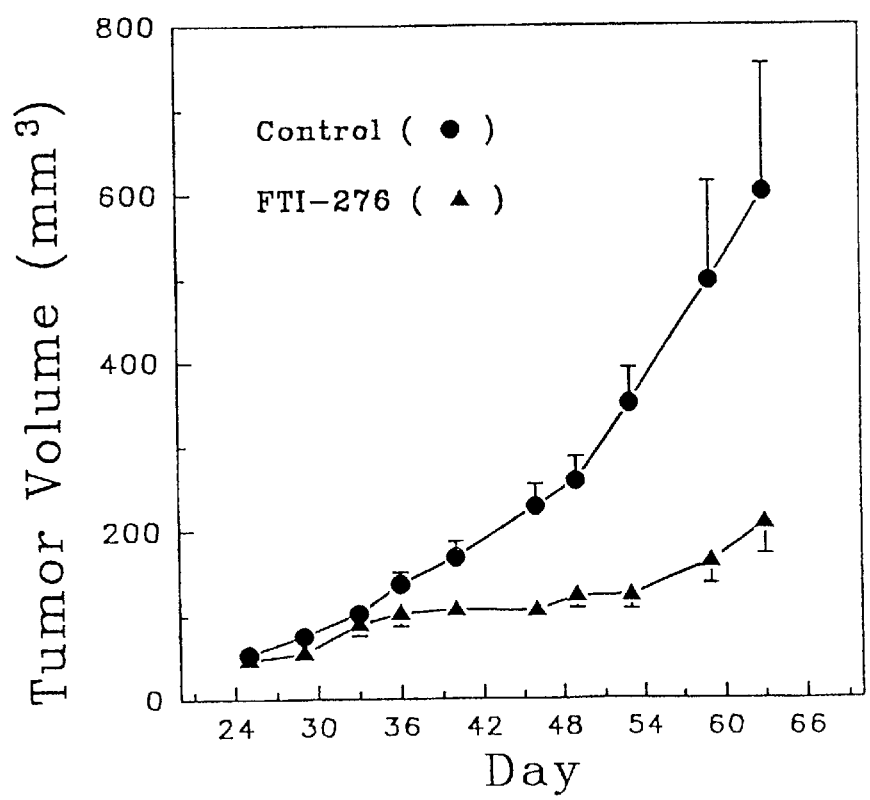

FIG. 8. Antitumor Efficacy of FTI-276 and FTI-277 in Human Lung Carcinoma (Calu-1) Cells.

Experimental procedure was the same as described in FIG. 7.

Figure 9A:
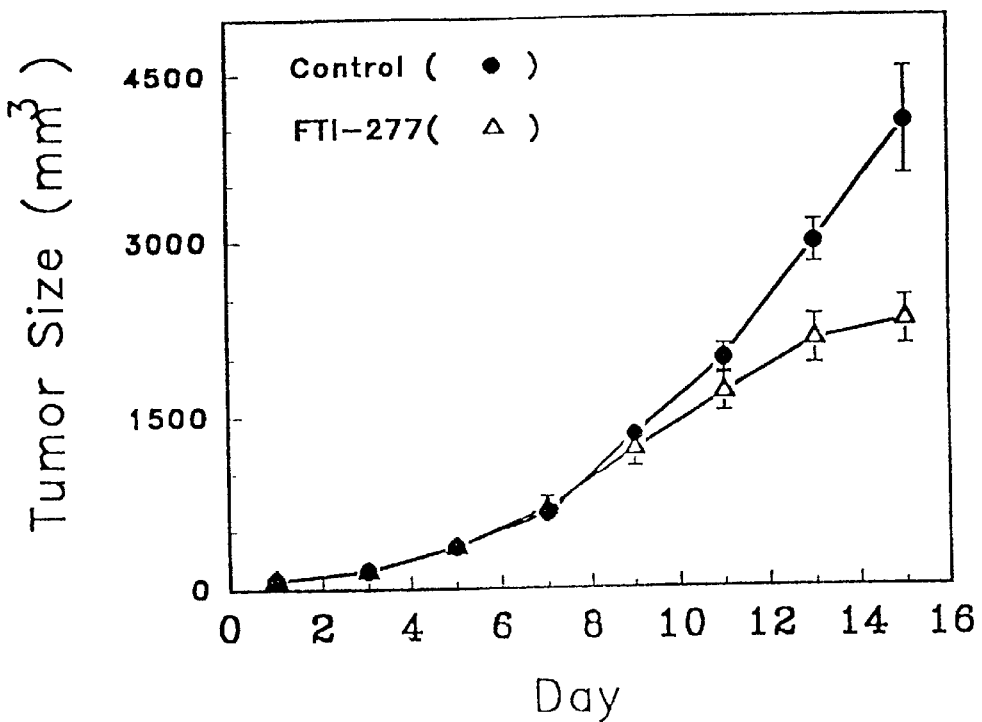
Figure 9B:
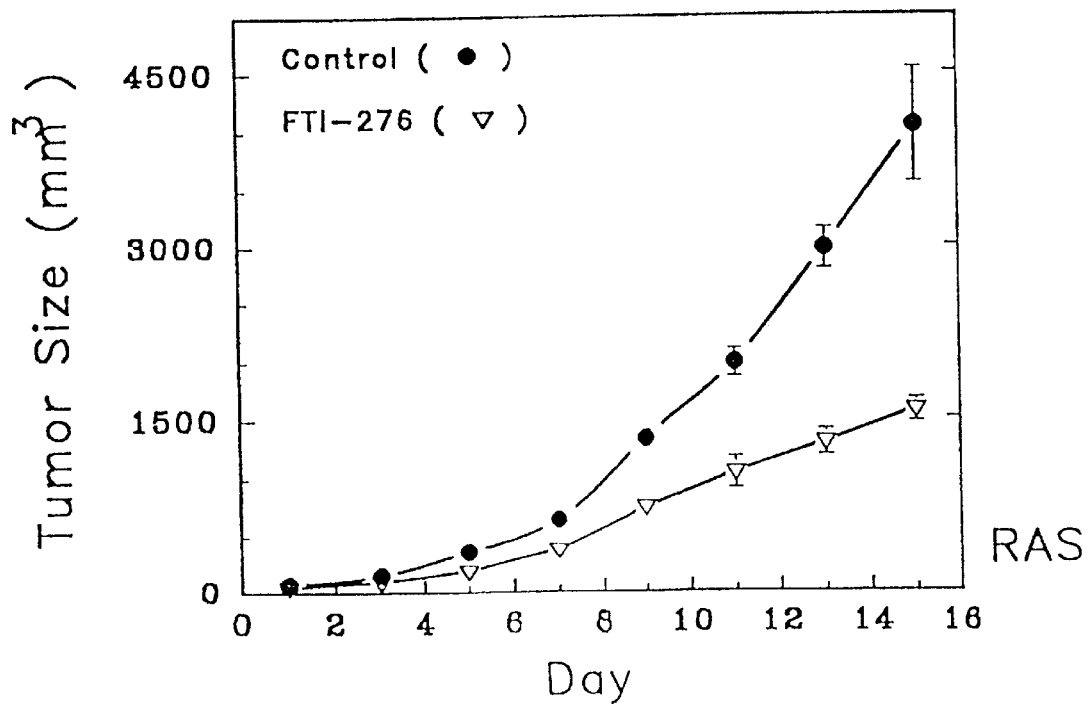

FIG. 9. Inhibition of Tumor Growth in Ras transformed cells by FTI-276 and FTI-277.

Ras-transformed NIH 3T3 cells were implanted subcutaneously into nude mice, and daily intraperitoneal injections with FTI-276 and FTI-277 (50 mg/kg) were started when the tumors reached 50 $mm^3$.

Figure 10A:
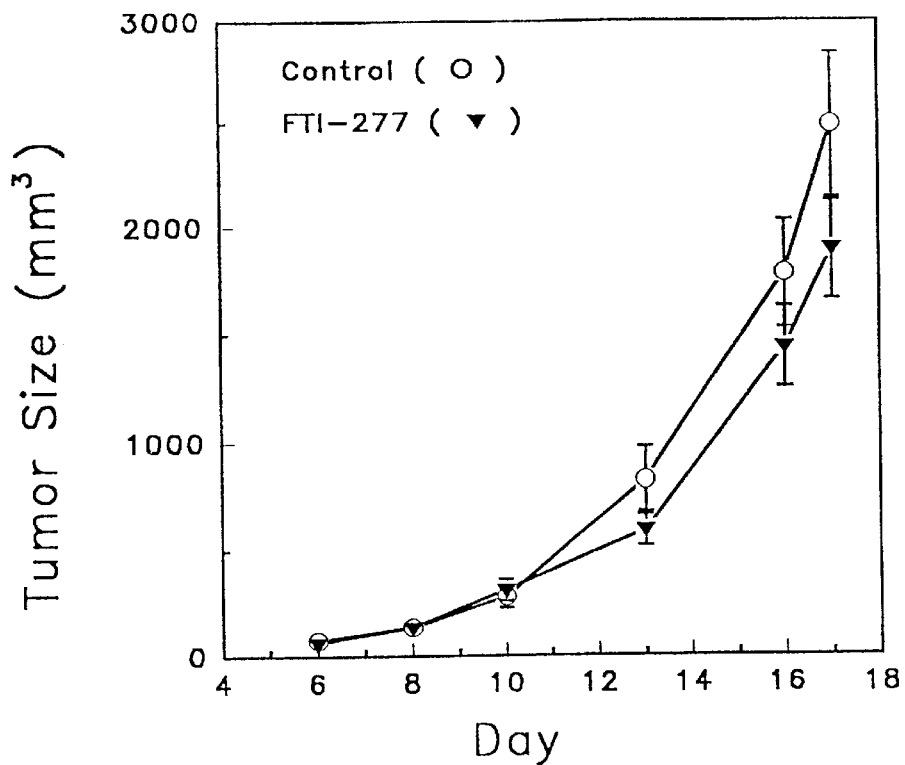
Figure 10B:
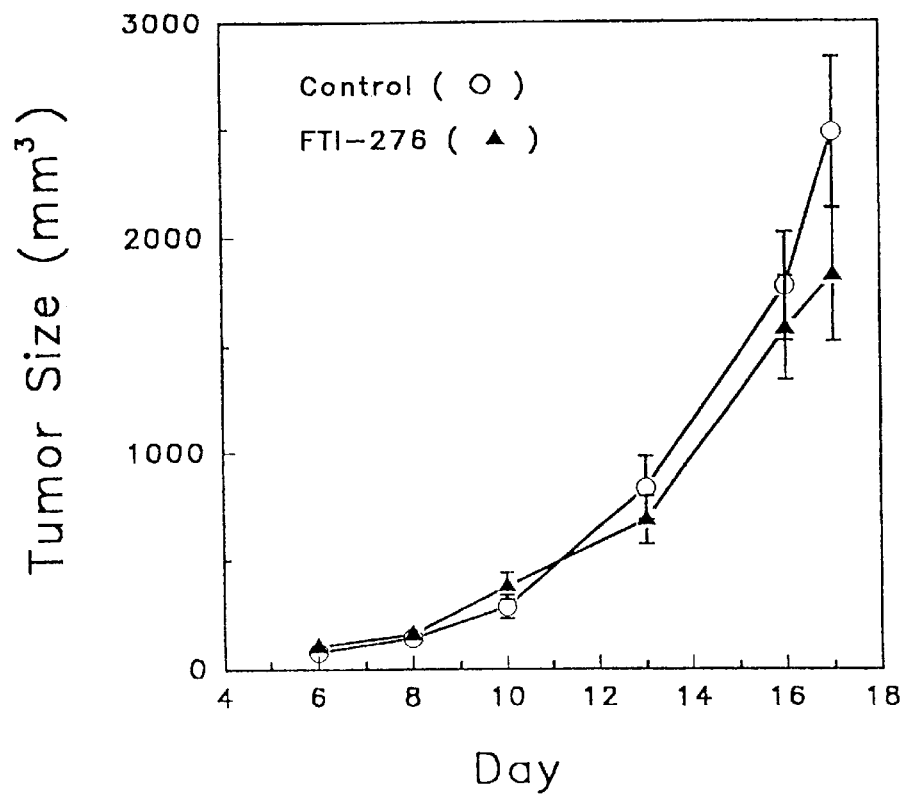

FIG. 10. Inhibition of Tumor Growth in Raf transformed cells by FTI-276 and FTI-277.

Raf-transformed NIH 3T3 cells were implanted subcutaneously into nude mice, and daily intraperitoneal injections with FTI-276 and FTI- 277 (50 mg/kg) were started when the tumors reached 50 $mm^3$.

Figure 11A:
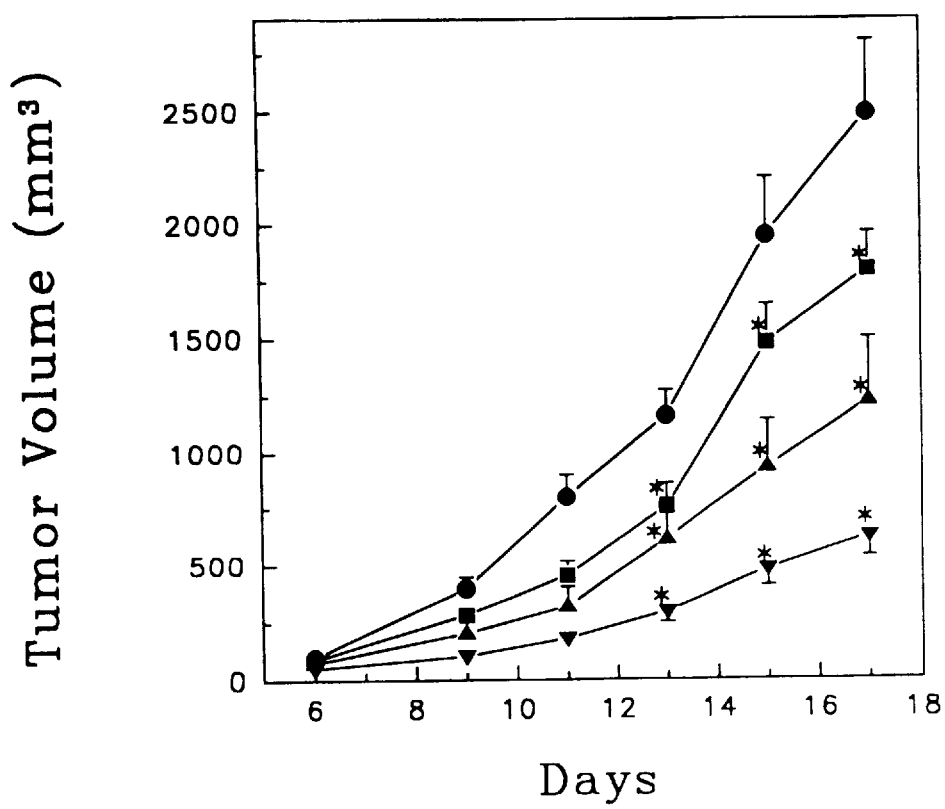
Figure 11B:
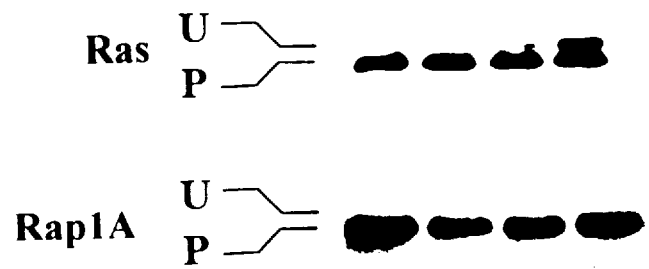

FIGS. 11A–11B. Dose response: Antitumor efficacy and Ras processing correlations.

Figure 1A:
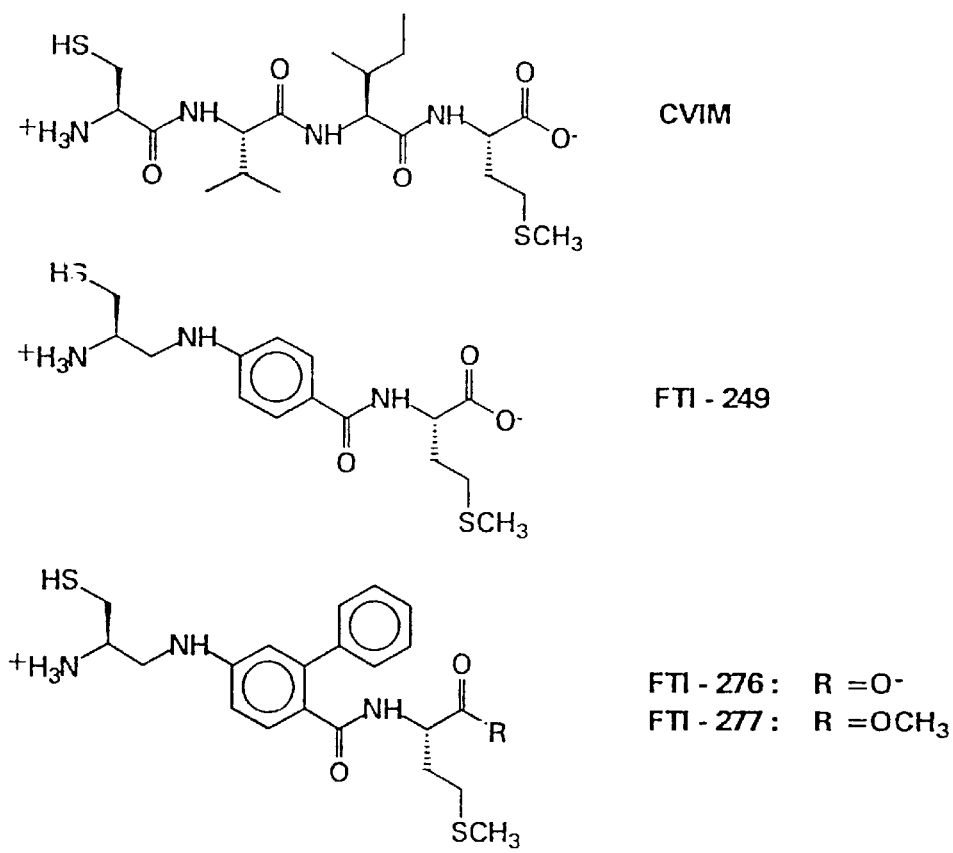
FIGS. 1A–1B: Ras CAAX peptidomimetics and FTase/GGTase I activities

A. Antitumor efficacy was carried out as described in FIG. 3 except that animals were randomly assigned to four groups each of 4 mice each (2 tumors per mouse). Saline treated groups (circles); FTI-276 treated groups: 10 mg/kg (squares), 50 mg/kg (upward triangles), 100 mg/kg (downward triangles). B. Ras processing was carried out 5 hours after the last treatement on day 17. Tumors were extracted from the animals, tissumized, and lysed in lysis buffer as described in FIG. 1. Lysates (25 μg) were electrophoresed on a 12.5% SDS-PAGE and immunoblotted with anti-Ras antibody Y13-238 as described previously. The blots were then reprobed with anti-Rap1A antibody (Santa Cruze Biotechnologies, Santa Cruz, Calif.).

DESCRIPTION OF PREFERRED EMBODIMENTS

For ease of reference, the following abbreviations may be used in the present specification:
FTase: farnesyltransferase;
GGTase: geranylgeranyltransferase;
SDS-PAGE: sodium dodecyl sulfate polyacrilamide gel electrophoresis
PBS: phosphate-buffered saline;
CAAX: tetrapeptide where C is cysteine, A is an aliphatic amino acid and X is any amino acid
DTT: dithiothreitol;
DOC: deoxycholate
BSA: bovine serum albumin The peptidomimetics of Formula (I) may be made using procedures which are conventional in the art. Preferably β is 2-phenyl-4-aminobenzoic acid although constrained derivatives such as tetrahydroisoquinoline-7-carboxylic acid, 2-aminomethyl pyridine-6-carboxylic acid or other heterocyclic derivatives, may also be used. We have previously disclosed compounds in which β is an aminomethylbenzoic acid (particularly 3-aminomethylbenzoic acid) in U.S. Pat. No. 5,602,098 which is hereby incorporated herein by reference. The acid component of β is conveniently reacted with cysteine so that the amino group of β and the cysteine carboxyl group react to form an amido group, other reactive substituents in the reactants being suitably protected against undesired reaction. In the case of the reduced-cysteine series of compounds, the amino group of β is reacted with a suitably protected cysteinal. The amino acid represented by X, preferably Met, is then reacted through its amino group with the deprotected and activated carboxyl group of spacer compound β. Following deprotection by removal of other protecting groups, the compound of Formula (I) is obtained.

As an alternative, β may first be reacted with the X amino acid followed by reaction with the cysteine or cysteinal component using conventional reaction conditions.

The invention also includes the pharmaceutically acceptable salts of the compounds of Formula (I). These may be obtained by reacting the free base or acid with the appropriate amount of inorganic or organic acid or base, e.g. an alkali metal hydroxide or carbonate, such as sodium hydroxide, an organic amine, e.g. trimethylamine or the like. Acid salts include the reaction products obtained with, for example, toluene sulfonic acid, acetic acid, propionic acid or the like as conventionally used in the art.

The compounds of the invention may be used to inhibit p21ras farnesyltransferase in any host containing the same. This includes both in vitro and in vivo use. Because the compounds inhibit farnesyltransferase, notably human tumor p21ras farnesyltransferase, and consequently inhibit the farnesylation of the oncogene protein ras, they may be used in the treatment of cancer or cancer cells. It is noted that many human cancers have activated ras and, as typical of such cancers, there may be mentioned colorectal carcinoma, myeloid leukemias, exocrine pancreatic carcinoma and the like.

The compounds of the invention may be used in pharmaceutical compositions of conventional form suitable for oral, subcutaneous, intravenous, intraperitoneal or intramuscular administration to a mammal or host. This includes, for example, tablets or capsules, sterile solutions or suspensions comprising one or more compounds of the invention with a pharmaceutically acceptable carrier and with or without other additives. Typical carriers for tablet or capsule use include, for example, lactose or corn starch. For oral compositions, aqueous suspensions may be used with conventional suspending agents, flavoring agents and the like.

The amount of inhibitor administered to obtain the desired inhibitory effect will vary but can be readily determined. For human use, daily dosages are dependent on the circumstances, e.g. age and weight. However, daily dosages of from 0.1 to 20 mg per kg body weight may be mentioned for purposes of illustration.

The various aspects of the invention are further described by reference to the following examples. These examples illustrate, among other things, the preparation of the present peptidomimetics and compounds compared therewith.

In the invention, the β component is, in general, any non-peptide amino acid combination or other hydrophobic spacer element that produces a compound which mimics the structure and conformation of CVIM or like tetrapeptides $CA_1A_2X$. A variety of hydrophobic spacers have been used as the β component according to this aspect of the invention. This includes, as examples, 3-aminobenzoic acid, 4-aminobenzoic acid and 5-aminopentanoic acid as well as heterocyclic carboxylic acids such as tetrahydroisoquinoline-7-carboxylic acid, 2-aminomethyl pyridine-6-carboxylic acid or the like as mentioned earlier, as replacements for the β component of the Formula (I) compounds. Thus, in a broad sense, the peptidomimetics of the invention include variants for Formula (I) where β stands for the radical of a non-peptide aminoalkyl or amino-substituted aliphatic or aromatic carboxylic acid or a heterocyclic monocarboxylic acid, for example, 3-aminobenzoic acid (3-ABA), 4-aminobenzoic acid (4-ABA) or 5-aminopentanoic acid (5-APA).

Other suitable β substituents which may be mentioned include those obtained by using aminomethyl- or aminocarboxylic acid derivatives of other cyclic hydrophobic compounds such as furan, quinoline, pyrrole, oxazole, imidazole, pyridine and thiazole. Generally speaking, therefore, the β substituent may be derived from any hydrophobic, non-peptidic aminoalkyl- or amino-substituted aliphatic, aromatic or heterocyclic monocarboxylic acid.

According to still another feature of the invention, other effective inhibitors for farnesyltransferase may be provided by incorporating a negatively charged residue onto the compounds of Formula (I). This feature of the invention is based on a consideration of the transition state of the farnesylation reaction and the recognition that the functional enzyme complex must involve a farnesyl pyrophosphate binding site close to the peptide binding region. Compounds representative of this embodiment include peptides prepared with a phosphonate residue linked at different distances to the cysteine sulfur. These derivatives have been prepared by reaction of N-Cbz-cysteine with ethyl 2-chloroethylphosphonate followed by condensation with the C-terminal methionine adduct of 4-aminobenzoic acid (or N-deprotected VIM methyl ester). Deprotection of the phosphonate, carboxylate and amino protecting groups gives analogs (5) and (6), respectively, which contain elements of the tetrapeptide and farnesyl pyrophosphate residues and hence are able to interact with binding groups in both recognition sites in p21ras farnesyltransferase:

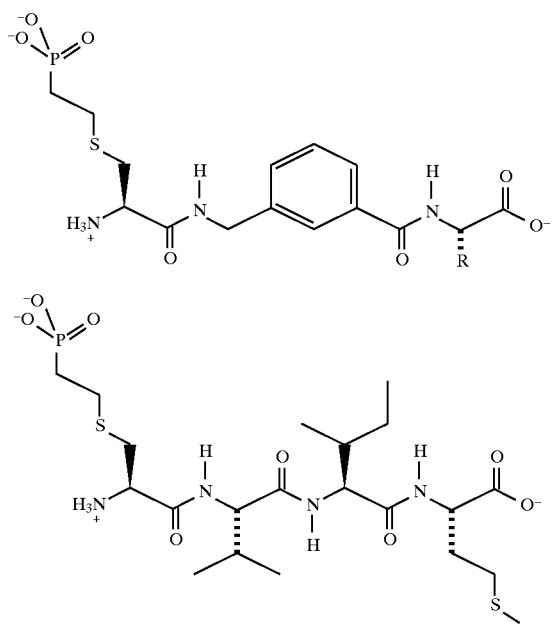

(5)

(6)

The above described phosphonates as contemplated herein can be structurally represented as follows:

A₁-C-β-X where C, X, β and A are as previously described and $A_1$ is a phosphonate group joined to cysteine through the cysteine sulphur atom.

As indicated earlier, an important further feature of the invention is the modification of the compounds of the invention, as well as the tetrapeptide p21ras farnesyl transferase inhibitors of the formula $CA_1A_2X$, to provide pro-drugs. This involves forming lipophilic esterase-sensitive derivatives from the compounds by appropriately functionalizing the terminal groups. For example, the terminal amino groups and the cysteine sulfur can be reacted with benzyl chloroformate to provide carbobenzyloxy ester end groups while the terminal carboxy group at the other end of the compound is converted to an alkyl or aryl ester, e.g. the methyl ester. Other examples include alkyl esters from 1 to 10 carbons in length, activated esters such as cyanomethyl or trifluoromethyl, cholesterol, cholate or carbohydrate derivatives. The term "lipophilic", when used in this context, is meant to include, inter alia, methoxycarbonyl and other long chain or carbamate groups. Examples of such groups are well known to the ordinarily skilled practitioner.

Derivatization of the prior peptides $CA_1A_2X$ and the peptidomimetics described herein with lipophilic or hydrophobic, esterase-sensitive moieties increases the plasma membrane permeability and cellular uptake of the compounds and consequently their efficiency in inhibiting tumor cell growth.

While the carbobenzyloxy derivatives have been referred to as one way of functionalizing the peptides and peptidomimetics to improve efficiency, it will be appreciated that a variety of other groups may also be used for the purposes noted. Typical alternatives include cholesterolyl, aryl or aralkyl such as benzyl, phenylethyl, phenylpropyl or naphthyl, or alkyl, typically methyl or other alkyl of, for example, up to 8 carbon atoms or more. It is contemplated that such functional groups would be attached to the cysteine sulfur and the terminal amino and carboxy groups.

Using C-ABA-M as representative of the present compounds, the functionalized pro-drug embodiment of the invention may be structurally illustrated as follows:

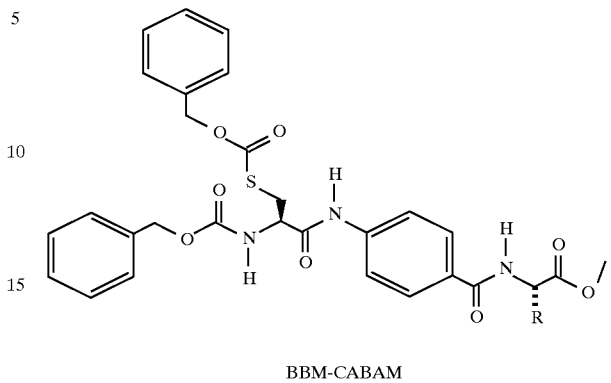

BBM-CABAM

In the above described BBM-compounds, the "BBM" used in the formulas represents a shorthand reference to the bis-(carboxybenzyloxy)methyl esters of CβM and CVIM.

The functionalized derivatives of the phosphonates described earlier herein are also useful cell growth inhibitors. Correspondingly, the "BMMM" designation used with compounds refers to the carboxy benzyloxy substitution and the three methyl groups in the methylated phosphoric and carboxylic acid end groups.

As noted, the purpose of the functional groups added to the parent compounds is to improve entry of the compounds into tumor cells. Once in the cells, the functional groups are removed to liberate the active compound to function in its inhibitory capacity.

As will be recognized by those in the art, the functionalized pro-drugs of the invention can be prepared using conventional and well-known procedures for esterifying amino, SH and carboxylic acid groups. Hence, details of such procedures are not essential for the preparation of the present pro-drugs.

EXAMPLE 1

SYNTHESIS OF FTI-232

N-BOC-4-aminobenzoic acid 4-amino-benzoic acid (10 g, 72.9 mmol) was placed into a mixture of dioxane (145.8 ml) and 0.5M NaOH (145.8 ml). The solution was cooled to 0° C. and di-t-butyl dicarbonate (23.87 g, 109.5 mmol) was added. The reaction mixture was allowed to warm to room temperature and stirred overnight. The next day, the dioxane was removed, the residue was made acidic and extracted into ethyl acetate. The ethyl acetate fractions were combined and washed with 1N HCl to remove any unreacted starting material. The solution was dried over $Na_2SO_4$ and the solvent was removed in vacuo. The crude material was recrystallized from ethyl acetate/hexanes to yield 12.2 g (70.6%) of pure product. mp 189°–190° C.; $^1$H NMR ($CD_3OD$) 1. 52 (9 H,s), 7.49 (2 H, d, J=8.6 Hz), 7.91 (2 H, d, J=8.6 Hz), 9.28 (1 H, s); $^{13}$C NMR ($CD_3OD$) 28.59, 81.29, 118.54, 125.30, 131.81, 145.70, 155.00, 169.80; anal. calc. for $C_{12}H_{15}NO_4$, C: 60.76, H: 6.37, N: 5.90; found, C: 60.52, H: 6.43, N: 5.83; HRMS calc. for $C_{12}H_{15}NO_4$, 237.0961, found, 237.1001.

N-BOC-4-aminobenzoyl methionine methyl ester

Into a dried, nitrogen filled flask was placed N-BOC-4-aminobenzoic acid (8.77 g, 36.97 mmol) in dry $CH_2Cl_2$ (148 ml) along with methionine methyl ester hydrochloride (8.12 g, 40.66 mmol). This solution was cooled in an ice bath and triethylamine (6.7 ml), EDCI (7.80 g, 40.66 mmol) and hydroxybenzotriazole (HOBT, 5.50 g, 40.66 mmol) were added. The mixture was stirred overnight, diluted with more $CH_2Cl_2$ and was extracted 3 times each with 1M HCl, 1M $NaHCO_3$ and water. The $CH_2Cl_2$ was dried over MgSO4 and the solvent was removed in vacuo. The solid was recrystallized from ethyl acetate/ hexanes to yield 9.72 g (71.3%) of pure product. mp 184°–185° C.; $^1$H NMR (CDCl$_3$) 1.53 (9 H, s), 2.06–2.18 (4 H, m), 2.23–2.33 (1 H, m), 2.59 (2 H, t, J=7.6 Hz), 3.80 (3 H, s), 4.92 (1 H, m), 7.45 (2 H, d, J=8.7 Hz), 7.77 (2 H, d, J=8.7 Hz); $^{13}$C NMR (CDCl$_3$) 15.59, 28.34, 30.15, 31.64, 52.10, 52.73, 81.20, 117.73, 127.8, 128.33, 141.88, 152.33, 166.50, 172.75; anal. calc. for $C_{18}H_{26}N_2O_5S$, C: 56.53, H: 6.85, N: 7.29; found, C: 56.47, H: 6.86, N: 7.29; m/ z (EI) 382 (M).

HCl -4-aminobenzoyl methionine methyl ester

N-BOC-4-aminobenzoyl methionine methyl ester (3.53 g, 9.59 mmol) was placed into $CH_2Cl_2$ (30–35 ml) and to it was added 3M HCl/Et$_2$O (38.4 ml). After standing a white precipitate formed. After 2 hours the solution was decanted, and the crystals were collected by centrifugation. The crystals were then washed several times with fresh ether and dried overnight on the vacuum pump. Meanwhile, the filtrate was left to stand overnight to allow additional product to precipitate. The second fraction was washed with ether and dried overnight on the vacuum pump. The total yield of pure fully deprotected material was 2.87 g (93.9%) yield. mp 158–164° C.; $^1$H NMR (CDCl$_3$) 2.10 (3 H, s), 2.12–b 2.29 (1 H, m), 2.52–2.71 (1 H, m), 2.59 (2 H, t, J=7.6 Hz), 3.75 (3 H, s), 4.79 (1 H, m), 7.02 (2 H, d, J=8.6 Hz), 7.55 (2 H, d, J=8.6 Hz); $^{13}$C NMR (CDCl$_3$) 15.23, 31.43, 31.53, 52.91, 52.43, 124.35, 130.56, 135.31, 135.76, 168.95, 173.87; HRMS calc. for $C_{13}H_{18}N_2O_3S$, 282.1038, found 282.1009.

N-BOC-S-trityl-cysteine-4-aminobenzoyl methionine methyl ester

N-BOC-S-trityl-Cys (2.86 g, 6.54 mmol) and triethylamine (1.2 ml) were placed into a dried, $N_2$ filled flask containing dry THF (104 ml). This was cooled to −10° C. using an ice/salt bath and isobutyl chloroformate (0.9 ml), IBCF, was added. The solution was stirred at −10° C. for 40 minutes and HCl-4-aminobenzoyl methionine methyl ester (2.08 g, 6.54 mmol) in dry $CH_2Cl_2$ (34.1 ml) with triethylamine (1.2 ml, 1.3 eq) was added. The solution warmed to room temperature and was stirred overnight under $N_2$. The solvent was then removed in vacuo and the residue was taken up in $CH_2Cl_2$ and extracted several times each with 1M HCl, $H_2O$ and brine (saturated NaCl). The organic layer was dried over $Na_2SO_4$ and the solvent was removed in vacuo. The pale yellow foam was then chromatographed on silica gel using a 2:1 hexanes, ethyl acetate elution mixture to yield 2.62 g (54.9%) of pure product. mp 110°–111° C.; $[\alpha]^{25}_D$=−8.0° (c=1, CH$_3$OH); $^1$H NMR (CDCl$_3$) 1.44 (9 H,s), 2.11–2.18 (4 H, m), 2.22–2.34 (1 H,m), 2.59 (2 H, t, J=7.4 Hz), 2.66–2.83 ( 2 H, m), 3.80 (3 H, s), 3.98 (1 H, m), 4.84 (1 H, m), 4.92 (1 H, m), 6.96 (1 H, d, J=7.7 Hz), 7.23–7.33 (9 H, m), 7.43–7.46 (6 H, m), 7.51 (2 H, d, J=8.5 Hz), 7.74 (2 H, d, J=8.5 Hz), 8.51 (1 H, s); $^{13}$C NMR (CDCl$_3$) 15.53, 28.34, 30.72, 30.89, 33.60, 52.23, 52.88, 54.95, 60.50, 67.13, 80.64, 118.81, 119.31, 126.94, 128.07, 128.30, 129.53, 141.06, 144.38, 156.31, 167.02, 170.13, 174.49; anal calc for $C_{40}H_{44}N_3O_6S_2 \cdot H_2O$, C: 64.50, H: 6.22, N: 5.64; found C: 64.14 H: 6.19, N: 5.56.

HCl-cysteine-4-aminobenzoyl methionine methyl ester

N-BOC-S-trityl-cysteine-4-aminobenzoyl methionine methyl ester (1 g, 1.37 mmol) was placed into a flask and taken up in $CH_3OH$ (13.7 ml). To this solution was added a solution of mercuric chloride (0.75 g, 2.74 mmol) in $CH_3OH$ (13.7 ml). Upon addition of the mercuric chloride, a white precipitate began to form. The mixture was heated on a steam bath at 65° C for 35 minutes and then it was cooled and the precipitate was filtered and washed sparingly with cold $CH_3OH$. After drying for several minutes on the filter, the solid was placed into a 50 ml 3-neck flask fitted with a gas inlet and outlet. Approximately 20–30 ml of $CH_3OH$ was added and $H_2S$ gas was bubbled through the heterogeneous solution for 30 minutes. Upon addition of the gas, the white solution turned orange and then black. The solution was centrifuged and the clear, colorless liquid was dried to give a white foam. This solid was placed on the vacuum pump for a short period and then was taken up in $CH_2Cl_2$ (10 ml) and the product was precipitated with a 3–4M HCl/Et$_2$O solution. The precipitate was collected by centrifugation and was washed with ether until pH was neutral. After drying under vacuum overnight, 0.38 g (66.5%) of product was obtained that was >95% pure by HPLC. mp foamed 141°–143° C., decomp 195° C.; $[\alpha]^{25}_D$=+3° (c=1, H$_2$O); $^1$H NMR (CD$_3$OD) 2.09 (3 H, s), 2.14–2.26 (1 H,m), 2.51–2.67 (3 H, m), 3.05 (1 H, dd, J=14.8 Hz, 7.3 Hz), 3.17 (1 H, dd, J=14.8 Hz, 4.8 Hz), 3.74 (3 H,s), 4.17 (1 H, J=7.3 Hz, 4.8 Hz ), 4.75–4.81 (1 H, m), 7.74 (2 H, d, J=8.6 Hz), 7.87 (2 H, d, J=8.6 Hz), 8.67 (1 H, d, J=8.4 Hz); $^{13}$C NMR (CD$_3$OD) 15.23, 26.38, 31.43, 31.56, 52.88, 53.30, 56.92, 120.46, 129.58, 130.75, 142.33, 166.91, 169.66, 174.06; anal calc for $C_{16}H_{24}ClN_3O_4S_2$, C: 45.55 H: 5.73, N: 9.96; found C: 45.31, H: 5.84, N: 9.79.

HCl-cysteine-4-aminobenzoyl methionine FTI232

HCl-cysteine-4-aminobenzoyl methionine methyl ester (0.51 g, 0.7 mmol) was taken up in THF (4.1 ml) and to this solution was added 0.5M LiOH (2.9 ml) at 0° C. The heterogeneous solution was stirred at 0C for 35–40 minutes and then the THF was removed in vacuo. The residue was taken up in $CH_2Cl_2$ and was washed three times with 1M HCl followed by brine. The organic solution was dried over $Na_2SO_4$ and the solvent was removed in vacuo. The pale yellow solid was taken up in 3 ml of $CH_2Cl_2$ and the product was precipitated with 3–4M HCl/Et$_2$O. The solid was collected by centrifugation, washed several times with ether until the ether washings were neutral and the process repeated until the HPLC appeared pure. A final yield of 78.6 mg (27.5%) of pure product was obtained. mp sub 157° C., decomp 211° C.; $[\alpha]^{25}_D$=+10° (c=0.8, H$_2$O); $^1$H NMR (CD$_3$OD) 2.09 (3 H, s), 2.17–2.32 (1 H,m), 2.53–2.66 (3 H, m), 3.06 (1 H, dd, J=14.6 Hz, 7.2 Hz), 3.19 (1 H, dd, J=14.6 Hz, 4.6 Hz), 4.21 (1 H, dd, J=7.23 Hz, 4.63 Hz), 4.73–4.78 (1 H, m), 7.75 (2 H, d, J=8.1 Hz), 7.87 (2 H, d, J=8.1 Hz); $^{13}$C NMR (CD$_3$OD) 15.23, 26.33, 31.58, 31.86, 53.24, 56.98, 120.48, 129.59, 131.10, 142.26, 166.89, 169.66, 175.29; anal calc for $C_{15}H_{22}ClN_3O_4S_2$, C: 44.16, H: 5.44, N: 10.30; found C: 45.45, H: 5.62, N: 10.03; m/ z (FAB) for free amine, 371 (M+1).

EXAMPLE 2

SYNTHESIS OF FTI-260

N-BOC-4-amino-3-methylbenzoic acid 4-amino-3-methylbenzoic acid (5 g, 33.1 mmol) was reacted according to the same procedure as N-BOC-4- aminobenzoic acid. The orange-brown solid was recrystallized from ethyl acetate and hexanes to yield 4.99 g (60%) of tan prismatic crystals. mp 180–182° C.; $^1$H NMR (CD$_3$OD) 1.51 (9 H, s), 2.27 (3 H, s), 7.66 (1 H, d, J=8.1 Hz), 7.79–7.82 (2 H, m), 8.32 (1 H, s); $^{13}$C NMR (CD$_3$OD) 17.98, 28.62, 81.47, 123.12, 127.05, 129.14, 130.65, 132.99, 142.45, 155.33, 168.70; anal calc for C$_{13}$H$_{17}$NO$_4$, C: 62.15, H: 6.82, N: 5.58; found C: 62.07, H: 6.86, N: 5.46; m/z (EI) 251; HRMS calc. for C$_{13}$H$_{17}$NO$_4$, 251.1158; found, 251.1153.

N-BOC-4-amino-3-methylbenzoyl methionine methyl ester

N-BOC-4-amino-3-methylbenzoic acid (2.00 g, 7.96 mmol) was reacted with methionine methyl ester hydrochloride (1.75 g, 8.76 mmol), EDCI (1.68 g, 8.76 mmol), HOBT (1.18 g, 8.76 mmol) and Et$_3$N (1.4 ml) in dry CH$_2$Cl$_2$ (31.8 ml) according to the procedure described for N-BOC-4-aminobenzoyl methionine methyl ester in Example 1. The crude material was recrystallized from ethyl acetate and hexanes to yield 2.61 g (85.7%) of pure product. mp 163°–165° C.; $^1$H NMR (CDCl$_3$) 1.54 (9 H,s), 2.06–2.18 (4 H, m), 2.23–2.34 (4 H, m), 2.59 (2 H, t, J=6.8 Hz), 3.80 (3 H, s), 4.92 (1 H, m), 6.45 (1 H, s), 6.88 (1 H, d, J=7.5 Hz), 7.63 (1 H, d, J=8.6 Hz), 7.66 (1 H, s), 8.05 (1 H, d, J=8.6); $^{13}$C NMR (CDCl$_3$) 15.47, 17.61, 28.22, 30.03, 31.55, 51.93, 52.57, 81.04, 118.73, 125.62, 127.66, 129.54, 139.89, 152.34, 166.58, 172.66.

HCl-4-amino-3-methylbenzoyl methionine methyl ester

N-BOC-4-amino-3-methylbenzoyl methionine methyl ester (0.99 g, 2.59 mmol) was dissolved in CH$_2$Cl$_2$ (15–20 ml) and precipitated with 3M HCl/Et$_2$O (20.7 ml). 0.83 g (96.6%) of pale orange precipitate was obtained after drying overnight on the vacuum pump. mp 157°–159° C.; $^1$H NMR (CD$_3$OD) 2.04 (3 H,s), 2.11–2.25 (1 H, m), 2.47 (3 H, s), 2.52–2.68 (3H. m), 3.74 (3 H, s), 4.75–4.80 (1 H, m), 7.48 (1 H, d, J=8.2 Hz), 7.81 (2 H, d, J=8.2 Hz), 7.87 (1 H, S); $^{13}$C NMR (CD$_3$OD) 15.23, 17.28, 31.43, 31.51, 52.91, 53.37, 124.41, 127.85, 131.99, 133.63, 134.14, 135.65, 169.05, 173.84; anal. calc. for C$_{14}$H$_2$N$_2$O$_3$S, C: 50.52, H: 6.36, N: 8.42; found C: 50.71, H: 6.40, N: 8.34.

N-BOC-S-trityl-cysteine-4-amino-3-methylbenzoyl methionine methyl ester

N-BOC-S-trityl-cysteine (0.55 g, 1.25 mmol) in dry THF (25 ml) was reacted with Et$_3$N (0.19 ml), IBCF (0.16 ml, 1.25 mmol) at –10° C. as described above. HCl-4-amino-3-methylbenzoyl methionine methyl ester (0.42 g, 1.25 mmol) in dry CH$_2$Cl$_2$ (6.5 ml) with Et$_3$N (0.26 ml) was added at –10° C and the reaction mixture was allowed to stir overnight under nitrogen. Workup was carried out as described above and the crude material was chromatographed on silica gel using a 2:1 mixture of hexanes and ethyl acetate as an elution mixture to give 0.12 g (13.9%) of pure product. mp 83°–85° C.; $[\alpha]^{25}{}_D$=–14.0° . (c=1, CH$_3$OH); $^1$H NMR (CDCl$_3$) 1.44 (9 H,s), 2.10–2.17 (4 H, m), 2.22–2.32 (4 H, m), 2.61 (2 H, t, J=6.57 Hz), 2.68–2.70 (1 H, m), 2.85–2.90 (1H. m), 3.79 (3 H,s), 3.93–4.08 (1 H, s), 4.84–4.88 (1 H, m), 4.90–4.95 (1 H, m), 6.95 (1 H, d, J=7.00 Hz), 7.20–7.33 (9 H,m), 7.39 (1 H, d, J=6.96 Hz), 7.44–7.47 (6 H,m), 7.59 (1 H, d, J=8.46 Hz), 7.65 1 H, s), 8.12 (1 H,d, J=8.22 Hz), 8.31 (1 H,s); $^{13}$C NMR (CDCl$_3$) 15.39 17.55, 27.70, 28.17, 30.00, 31.43, 31.41, 51.90, 52.51, 59.95, 67.30. 80.74, 84.54, 120.74, 125.33, 126.70, 126.83, 127.89, 128.00, 129.40, 138.92, 144.22, 166.50, 166.89, 168.87, 172.56.

TFA-cysteine-4-amino-3-methylbenzoyl methionine FTI260

N-BOC-S-trityl-cysteine-4-amino-3-methylbenzoyl methionine methyl ester (0.27 g, 0.37 mmol) in THF (2.1 ml) was deprotected with 0.5M LiOH (2.9 ml) over 1.5 h at room temperature. The solvent was removed in vacuo and the residue was taken up in CH$_2$Cl$_2$ and extracted 3 times with 1N HCl followed by extraction with brine. The organic solution was dried over Na$_2$SO$_4$ and the solvent was removed in vacuo to give 0.19 g (73.5%) of the free acid. The free acid was then taken up in CH$_2$Cl$_2$ (1.4 ml) and Et$_3$SiH (0.04 ml) was added followed by trifluoroacetic acid, TFA (1.4 ml). The reaction mixture was stirred at room temperature for 1 hour. The TFA was removed and the residue was dissolved in H$_2$O and extracted with Et$_2$O until all of the trityl derivative was removed. The water was lyophilized and a crude HPLC showed that the material was impure and contained diastereomers. The product was purified on the preparative HPLC using 0.1% TFA in water and acetonitrile elution mixture to give 2 diastereomers and only the major component (determined according to the major compound in the HPLC trace) was characterized. mp sub 112° C., foamed 158–163° C., decomp 196–197° C.; $[\alpha]^{25}{}_D$=+12.7°(c=0.6 H$_2$O) , $[\alpha]^{25}{}_D$=+21.0° (c=1 H$_2$O); $^1$H NMR (CD$_3$OD) 2.09–2.17 (4 H, m), 2.19–2.30 (1 H, m), 2.36 (3 H, s), 2.57–2.65 (2 H, m), 3.08 (1 H, dd, J=14.6 Hz, 6.9 Hz), 3.19 (1 H, dd, J=14.6 Hz, 5.2 Hz), 4.25(1 H, dd, J=6.9, 5.2 Hz), 4.70–4.75 (1 H, m), 7.64 (1 H, d, J=8.4 Hz), 7.69–7.73 (1 H, m), 7.77 (1 H, s); $^{13}$C NMR (CD$_3$OD) 15.23, 18.28, 26.54, 31.58, 32.06, 53.53, 56.66, 125.54, 125.77, 126.74, 131.04, 133.24, 139.26, 167.53, 169.70, 175.59.

EXAMPLE 3

SYNTHESIS OF FTI-261

N-BOC-4-amino-3-methoxybenzoic acid 4-amino-3-methoxybenzoic acid (1 g, 5.98 mmol) was reacted with di-t-butyl dicarbonate (1.96 g, 6.58 mmol) in dioxane (12 ml) and 0.5M NaOH (12 ml) according to the same procedure as N-BOC-4-aminobenzoic acid. 1.50 g (93.7%) of tan crystals were obtained after recrystallization from ethyl acetate and hexanes. mp 176°–178° C.; $^1$H NMR (CD$_3$OD) 1.52 (9 H, s), 3.92 (3 H, s), 7.56 (1 H, s), 7.62 (1 H, d, J=8.4 Hz), 7.96 (1 H, s), 8.03 (1 H, d, J=8.4 Hz); $^{13}$C NMR (CD$_3$OD) 28.53, 56.35, 81.78, 112.01, 118.58, 124.20, 125.76, 133.84, 149.04, 154.20, 169.60; HRMS calc. for C$_{13}$H$_{17}$NO$_5$ 267.1107; found, 267.1103.

N-BOC-4-amino-3-methoxybenzoyl methionine methyl ester

N-BOC-4-amino-3-methoxybenzoic acid (0.35 g, 1.31 mmol) was reacted with methionine methyl ester hydrochloride (0.9 g, 1.43 mmol) using EDCI as in N-BOC-4-aminobenzoyl methionine methyl ester. After recrystallization from ethyl acetate and hexanes, 0.36 g (57.2 %) of pure product was obtained. mp 163°–165° C.; $^1$H NMR (CDCl$_3$) 1.53 (9 H, s), 2.09–2.18 (4 H, m), 2.23–2.35 (1 H, m), 2.60 (2 H, t, J=6.9 Hz), 3.80 (3 H, s), 3.93 (3 H, s), 4.92 (1 H, br s), 6.93 (1 H, d, J=7.6 Hz), 7.25 (1 H, m), 7.31 (1 H, d, J=10.2 Hz), 7.44(1 H, s), 8.15(1 H, d, J=8.5 Hz); $^{13}$C NMR (CDCl$_3$) 15.47, 28.23, 30.09, 31.48, 52.06, 52.54, 55.81, 80.82, 98.06, 109.38, 116.66, 119.31, 131.52, 147.23, 152.31, 166.57, 172.58; m/z (FAB) 413 (M+1).

HCl-4-amino-3-methoxybenzoyl methionine methyl ester

N-BOC-4-amino-3-methoxybenzoyl methionine methyl ester (0.71 g, 1.79 mmol) was taken up in $CH_2Cl_2$ (4 ml) and precipitated with 3–4M HCl/ $Et_2O$ (12 ml). The precipitate was washed as usual with $Et_2O$ and dried overnight under vacuum to result in 0.55 g (88.3%) of reddish material. mp 176°–177° C.; $^1$H NMR ($CD_3OD$) 2.08 (3 H, s) , 2.21 (2 H, m), 2.61 (2 H, m), 3.74 (3 H, s), 4.02 (3 H, s), 4.79 (1 H, m), 7.50 (1 H, d, J=8.2 Hz), 7.57 (1 H, d, J=4.1 Hz) 7.67 (1 H, s); $^{13}$C NMR ($CD_3OD$) 15.26, 31.34, 31.42, 52.95, 53.38, 57.12, 112.29, 121.43, 124.57, 124.77, 136.15, 153.67, 168.79, 173.81.

N-BOC-S-trityl-cysteine-4-amino-3-methoxybenzoyl methionine methyl ester

N-BOC-S-trityl-cysteine (0.76 g, 1.74 mmol) in dry THF (27.5 ml) was reacted with $Et_3N$ (0.24 ml), IBCF (0.23 ml, 1.74 mmol) at –10° C. as described above. HCl-4-amino-3-methoxybenzoyl methionine methyl ester (0.55 g, 1.58 mmol) in dry $CH_2Cl_2$ ( 8.7 ml) with $Et_3N$ (0.30 ml) was added to the mixture and was allowed to stir overnight under nitrogen. It was worked up as described for N-BOC-S-trityl-cysteine-4-aminobenzoyl methionine methyl ester in Example 1, and the crude material was chromatographed on silica gel using a 2:1 mixture of hexanes and ethyl acetate to give 0.18 g (15.2%) of pure product. $^1$H NMR ($CDCl_3$) 1.45 (9 H, s), 2.05–2.33 (5 H, m), 2.57–2.65 (2 H, m), 2.68–2.72 (1 H, m), 2.75–2.96 (1 H, m), 3.78 (3 H, s), 3.84 (3 H, s), 4.90–5.00 (1 H, m), 5.03–5.18 (1 H, m), 7.17–7.48 (17 H, m), 8.30–8.38 (1 H, m), 8.65 (1 H, br s).

TFA-Cysteine-4-amino-3-methoxybenzoyl methionine FTI-261

N-BOC-S-trityl-cysteine-4-amino-3- methoxybenzoyl methionine methyl ester (0.18 g, 0.24 mmol) was deprotected with LiOH at room temperature as described above to give the free acid. The free acid was then further deprotected in $CH_2Cl_2$ (1.2 ml) with $Et_3SiH$ (0.04 ml, 0.24 mmol) and TFA (1.2 ml). The product was worked up as described for HCl-cysteine-4-aminobenzoyl methionine in Example 1, and HPLC revealed that the product was impure. The crude material was then purified on the HPLC using 0.1% TFA in water and acetonitrile as eluting solvents to result in two pure samples that were expected to be diastereomers. The major component (determined according to the major compound in the HPLC trace) was characterized as follows. mp sub 109° C., decomp 191°–193° C.; $[\alpha]^{25}_D$=–30.0° (c=1, $H_2O$), $[\alpha]^{25}_D$=+19.0° (c=1, $H_2O$); $^1$H NMR ($CD_3OD$) 2.10 (3 H, s), 2.12–2.18 (1 H, m), 2.20–2.32 (1 H, m), 2.53–2.71 (2 H, m), 3.00 (1 H, dd, J=14.6, 7.5), 3.15 (1 H, dd, J=14.58, 4.8), 4.77 (1 H, dd, J=7.5, 4.8), 7.50 (1 H, d, J=8.4 Hz), 7.56 (1 H, s), 8.23 (1 H, d, J=8.4 Hz); $^{13}$C NMR ($CD_3OD$) 15.20, 26.65, 31.60, 31.76, 53.27, 56.58, 56.76, 111.04, 121.08, 122.14, 130.85, 131.85, 150.88, 167.21, 169.61, 175.36; m/ z (FAB) for free amine, 402 (M+1).

EXAMPLE 4

SYNTHESIS OF FTI-272

4-nitro-2-phenyltoluene 2-bromo-4-nitrotoluene (2.16 g, 10.00 mmol) and phenyl boric acid (1.46 g, 12.00 mmol) were dissolved into anhydrous DMF (25 ml) under nitrogen. To this mixture was added $Pd(Ph_3P)_4$ (0.58 g, 5%). The mixture was heated at 100° C. overnight. The solution was poured onto 1N HCl and extracted with $Et_2O$. The crude material was chromatographed on silica gel using hexanes as an eluent. After recrystallization from ethanol, 1.23 g (57.6%) of pale orange needles were obtained. mp 69°–71° C.; $^1$H NMR ($CDCl_3$) 2.36 (3 H, s), 7.29–7.40 (2 H, m), 7.41–7.49 (5 H,m), 8.07–8.10 (2 H, m); $^{13}$C NMR ($CDCl_3$) 20.68, 121.96, 124.51, 127.78, 128.41, 128.83, 131.06, 139.44, 142.97, 143.48, 146.05; anal calc. for $C_{13}H_{11}NO_2$ C:73.26, H:5.20, N:6.57; found, C:73.10, H:5.12, N:6.50; m/ z (EI) 213; HRMS calc. for $C_{13}H_{11}NO_2$, 213.0790; found, 213.0793.

4-nitro-2-phenylbenzoic acid 4-nitro-2-phenyltoluene (0.50 g, 2.34 mmol) was dissolved in water (4.6 ml) and pyridine (2.3 ml). The mixture was heated to reflux and $KMnO_4$ (1.85 g, 11.70 mmol) was added. The reaction mixture was heated overnight and the solution was filtered and washed several times with boiling water. The aqueous solution was made acidic and the product was extracted into ethyl acetate. The ethyl acetate was dried over $Na_2SO_4$ and the solvent removed in vacuo to result in 0.37 g (67.9%) of pure yellow product. mp 174°–176° C.; $^1$H NMR ($CD_3OD$) 7.38–7.48 (5 H, m), 7.96 (1 H, d, J=8.5 Hz), 8.21 (1 H, d, J=2.3 Hz), 8.28 (1 H, dd, J=8.48, 2.37); $^{13}$C NMR ($CD_3OD$) 122.95, 126.09, 129.27, 129.42, 129.49, 131.56, 139.26, 140.42, 144.41, 150.17, 170.52; m/ z (EI) 243 (M).

4-nitro-2-phenylbenzoyl methionine methyl ester 4-nitro-2-phenylbenzoic acid (0.30 g, 1.23 mmol), methionine methyl ester hydrochloride salt (0.27 g, 1.35 mmol), EDCI (0.26 g, 1.35 mmol), HOBT ( 0.18 g, 1.35 mmol) and $Et_3N$ (0.19 ml) in dry $CH_2Cl_2$ (4.9 ml) were reacted according to the above procedure and worked up as described for N-BOC-4-aminobenzoyl methionine methyl ester in Example 1. After recrystallization from ethyl acetate and hexanes, 0.41 g (85.5%) of pure product was isolated. mp 98°–101° C.; $^1$H NMR ($CDCl_3$) 1.62–1.73 (1 H, m), 1.79–1.88 (1 H, m), 1.91 (3 H, s), 1.99 (2 H, t, J=7.2 Hz), 3.59 (3 H, s), 4.53 (1 H, m), 6.45 (1 H, d, J=7.8 Hz), 7.33–7.40 (5 H, m), 7.67 (1 H, d, J=8.3 Hz), 8.07–8.12 (2 H, m); $^{13}$C NMR ($CDCl_3$) 14.92, 29.11, 30.67, 51.51, 52.29, 121.86, 124.74, 128.27, 128.60, 128.69, 129.52, 137.50, 140.56, 141.02, 148.09, 167.23, 171.23; m/ z (FAB) , 389 (M+1).

4-amino-2-phenylbenzoyl methionine methyl ester 4-nitro-2-phenylbenzoyl methionine methyl ester (0.35 g, 0.90 mmol) was taken up in ethyl acetate (9.0 ml). To this mixture was added $SnCl_2 \cdot 2H_2O$ (1.02 g, 4.50 mmol) and the reaction was heated under nitrogen at reflux for 1h. The mixture was poured onto ice, the solution was made basic using $NaHCO_3$ and the product was extracted into ethyl acetate several times (7–8). The ethyl acetate fractions were combined washed with brine and dried over $Na_2SO_4$ and the solvent was removed in vacuo to give 0.24 g (73.4%) of yellow solid. $^1$H NMR ($CDCl_3$) 1.58–1.70 (1 H, m), 1.80–1.92 (1 H, m), 1.98 (3 H, s), 2.06 (2 H, t, J=7.7 Hz), 3.62 (3 H, s), 4.00 (2 H, br s), 4.56–4.63 (1 H, m), 5.84 (1 H, d, J=7.7 Hz), 6.50 (1 H, s), 6.61 (1 H, d, J=8.4 Hz), 7.29–7.42 (5 H, m), 7.58 (1 H, d, J=8.3 Hz); $^{13}$C NMR ($CDCl_3$) 15.02, 29.25, 31.25, 51.57, 52.15, 113.27, 115.88, 123.52, 127.56, 128.37, 128.44, 130.92, 140.66, 141.44, 148.53, 168.58, 171.91.

N-BOC-S-trityl-cysteine-4-amino-2-phenylbenzoyl methionine methyl ester

N-BOC-S-trityl-cysteine (0.31 g, 0.66 mmol) in dry THF (11 ml) was reacted with $Et_3N$ (0.10 ml), IBCF (0.09 ml, 0.73 mmol) at −10° C. as described for N-BOC-S-trityl-cysteine-4- aminobenzoyl methionine methyl ester in Example 1. 4-amino-2-phenylbenzoyl methionine methyl ester (0.24 g, 0.66 mmol) in dry $CH_2Cl_2$ (3.5 ml) was added and the mixture was allowed to stir overnight under nitrogen. It was worked up as described as further described for N-BOC-S-trityl-cysteine-4- aminobenzoyl methionine methyl ester in Example 1, and after drying the crude material was chromatographed on silica gel using a 2:1 mixture of hexanes and ethyl acetate to give 84.70 mg (16.0%) of pure product. mp 100°–103° C.; $^1H$ NMR ($CDCl_3$) 1.41 (9 H,s), 1.61–1.78 (1 H, m), 1.84–1.95 (1 H, m), 2.00 (3 H, s), 2.05 (2 H, t, J=7.6 Hz), 2.63 (1 H, dd, J=12.7 Hz, 6.9 Hz), 2.72 (1 H, dd, J=12.7 Hz, 5.51 Hz), 3.64 (3 H, s), 4.02 (1 H, br s), 4.58–4.63 (1 H, m), 4.90 (1 H, d, J=7.4 Hz), 6.10 (1 H, d, J=6.6 Hz), 7.18–7.30 (10 H, m), 7.37–7.44 (11 H, m), 7.50 (1 H, s), 7.58 (1 H, d, J=8.2 Hz), 8.69 (1 H, s); $^{13}C$ NMR ($CDCl_3$) 15.21, 28.20, 29.38, 31.24, 33.00, 51.77, 52.35, 54.15, 67.30, 80.85, 118.18, 120.86, 126.88, 127.90, 128.03, 128.56, 128.66, 129.44, 129.79, 130.14, 156.00, 168.52, 169.11, 171.85.

TFA Cysteine-4-amino-2-phenylbenzoyl methionine

FTI-272

N-BOC-S-trityl-cysteine-4-amino-2- phenylbenzoyl methionine methyl ester (84.70 mg, 0.11 mmol) of was taken up in THF (0.62 ml) and to this was added 0.5M LiOH (0.32 ml) at 0° C. The mixture was stirred at 0° C. for 35 minutes. The solvent was removed in vacuo using a cold water bath on the rotovap. The residue was worked up as described for HCl-cysteine-4-aminobenzoyl methionine in Example 1, and 60 mg of the free acid was obtained. This was then dissolved into $CH_2Cl_2$ (0.8 ml) and $Et_3SiH$ (0.01 ml) was added followed by TFA (0.8 ml). The reaction mixture was stirred at room temperature for 1 h and worked up as described for TFA-cysteine-4-amino-3- methylbenzoyl methionine in Example 2. After lyophilization, 0.0387 g (84.0%) was obtained. HPLC revealed that no epimerization had occurred, however the material was purified on the HPLC to eliminate baseline impurities. mp 150°–154 C.; $[\alpha]^{25}_D$=+21.5° (c=0.7, $H_2O$ $CH_3OH$); $^1H$ NMR ($CD_3OD$) 1.62–1.79 (1 H, m), 2.00–2.10 (5 H, m), 2.16–2.18 (1 H, m), 3.03 (1 H, dd, J=14.7 Hz, 7.3 Hz), 3.15 (1 H, dd, J=14.7 Hz, 4.8 Hz), 4.46 (1 H, br s), 7.37–7.41 (5 H, m), 7.52–7.55 (1 H, m), 7.65–7.67 (2 H, m); $^{13}C$ NMR ($CD_3OD$) 15.03, 26.35, 31.78, 32.79, 57.01, 119.40, 122.35, 128.95, 129.62, 129.71, 130.15, 133.49, 140.50, 141.36, 142.53, 167.05, 167.76, 172.51; anal. calc. for $C_{23}H_{26}F_3N_3O_6S_2$, C: 49.20, H: 4.67, N: 7.48; found, C: 49.14 H: 4.71, N: 7.42.

EXAMPLE 5

HCl cysteine-4-amino-2-phenylbenzoyl methionine methyl ester FT1274

N-BOC-S-trityl-cysteine-4-amino-2-phenylbenzoyl methionine methyl ester (0.06 g, 0.075 mmol) was dissolved into methanol (2 ml) and to it was added $HgCl_2$ (0.04 g) in methanol (1 ml). The reaction was carried out as described above to yield 15.7 mg of slightly impure compound by HPLC. mp 130°–132° C.; $^1H$ NMR ($CD_3OD$) 1.72–1.84 (1 H, m), 1.90–2.24 (6 H, m), 3.05 (1 H, dd, J=14.6 Hz, 8.5 Hz), 3.19 (1 H, dd, J=14.6 Hz, 3.6 Hz), 3.69 (3 H, s), 4.22 (1 H, dd, J=.5 Hz, 3.6 Hz), 4.48–4.53 (1 H, m), 7.33–7.43 (5 H, m), 7.51 (1 H, d, J=8.9 Hz), 7.70–7.72 (2 H, m); $^{13}C$ NMR ($CD_3OD$) 15.04, 26.36, 30.88, 31.36, 52.85, 53.05, 56.93, 119.42, 122.38, 128.88, 129.55, 129.73, 130.05, 133.17, 140.55, 141.32, 142.52, 166.92, 172.61, 173.58; anal. calc. for $C_{24}H_{29}ClN_3O_6S_2·H_2O$, C: 51.20, H: 5.86, N: 8.14; found, C: 51.23 H: 5.60, N: 8.22.

EXAMPLE 6

SYNTHESIS OF FTI-275

2-bromo-4-nitrobenzoic acid 2-bromo-4-nitrotoluene (5.00 g, 23.14 mmol) was dissolved into pyridine ( 23 ml) and water (46 ml). The heterogeneous mixture was heated to 60 ∞C and $KMnO_4$ (18.29 g, 115.7 mmol) was added carefully. The mixture was then heated under reflux overnight. The reaction mixture was filtered and washed with boiling water. The solution was then made acidic and extracted into ethyl acetate, dried over $Na_2SO_4$, and the solvent was removed in vacuo. A crude NMR revealed remaining starting material so the solid was taken up in NaOH and washed with hexanes. The aqueous phase was made acidic and the product was extracted into ethyl acetate. The ethyl acetate fractions were combined and dried over $Na_2SO_4$ and the solvent was removed in vacuo to yield 3.72 g (65.4%). mp 158°–160C.; $^1H$ NMR ($CD_3OD$) 7.81 (1 H, d, J=8.5 Hz), 8.08 (1 H, d, J=8.5 Hz), 8.30 (1 H, s); $^{13}C$ NMR ($CD_3OD$) 121.96, 122.75, 129.36, 132.24, 139.52, 149.54, 167.75; anal. calc. for $C_7H_4BrNO_4$+0.1 ethyl acetate, C: 34.88, H: 1.90, N: 5.50; found, C: 34.68, H: 1.86, N: 5.82.

3,5-dimethylphenyl boronic acid

Mg turnings (1.44 g, 59.43 mmol) were covered with dry THF (18.8 ml) in a dried, $N_2$ filled flask fitted with an addition funnel and reflux condenser. To this was added 5-bromo-m-xylene (10 g, 54.03 mmol) in THF (15 ml) after initiation of the Grignard reaction. The addition was carried out over several minutes and the reaction mixture was heated at reflux for 1–2 h until most of the Mg had reacted. The reaction mixture was then cooled and transferred to an addition funnel fitted to a $N_2$ filled flask containing triisopropyl borate (24.9 ml) at −70° C. The dropwise addition was carried out over several minutes and the mixture warmed to room temperature and stirred overnight. The grey solution was poured onto 2M HCl and immediately turned yellow. The solution was extracted into $Et_2O$ and the $Et_2O$ fractions were combined, dried over $MgSO_4$ and the solvent was removed in vacuo to yield 2.41 g (29.7%). mp 249–251° C.; $^1H$ NMR ($CDCl_3$) 2.44 (6 H, s), 7.23 (1 H, s), 7.84 (2 H, s); $^{13}C$ NMR ($CD_3OD$) 21.36, 133.28, 134.39, 137.48.

4-nitro-2-(3,5-dimethylphenyl)benzoic acid 2-bromo-4-nitrobenzoic acid (0.50 g, 2.03 mmol) and 3,5-dimethylphenyl boronic acid (0.34 g, 2.23 mmol) were dissolved into anhydrous DMF (dimethylformamide) (25 ml) under nitrogen. To this mixture was added $Cs_2CO_3$ (1.66 g, 5.08 mmol) followed by $Pd(Ph_3P)_4$ (0.12 g, 5%). The mixture was heated at 100° C. overnight. The solution was poured onto 1N HCl and extracted into $Et_2O$. It was dried over $MgSO_4$ and the solvent was removed in vacuo. The crude material was chromatographed on silica gel using a 9:1 mixture of hexanes and ethyl acetate to yield 0.34 g (61.7%) of pure product. $^1H$ NMR ($CDCl_3$) 2.36 (6 H, s), 6.99 (2 H, s), 7.07 (1 H, s), 8.03 (1 H, d, J=9.0 Hz), 8.23–8.25 (2 H, m); $^{13}C$ NMR ($CDCl_3$) 21.28, 121.68, 123.68, 125.74, 126.07, 130.22, 131.19, 131.31, 135.04, 138.21, 144.74, 170.75.

4-nitro-2-(3,5-dimethylphenyl)benzoyl methionine methyl ester 4-nitro-2-(3,5-dimethylphenyl)benzoic acid (0.15 g, 0.55 mmol), methionine methyl ester hydrochloride salt (0.11 g, 0.55 mmol), EDCI (0.11 g, 0.55 mmol), HOBT (0.07 g, 0.55 mmol) and Et$_3$N (0.08 ml) in dry CH$_2$Cl$_2$ (2.2 ml) were reacted and worked up according to the procedure for N-BOC-4-aminobenzoyl methionine methyl ester in Example 1. After recrystallization from ethyl acetate and hexanes, 0.13 g (58.4%) of pure product was isolated. mp 122–124° C.; $^1$H NMR (CDCl$_3$) 1.2–1.84 (1 H, m), 1.85–1.97 (1 H, m), 2.01 (3 H, s), 2.05 (3 H, t, J=7.7 Hz), 2.38 (6 H, s), 3.70 (3 H, s), 4.67–4.74 (1 H, m), 6.03 (1 H, d, J=7.9 Hz), 7.05 (2 H, s), 7.09 (1 H, s), 7.84–7.87 (1 H, m), 7.84–7.87 (1 H, m), 8.23–8.26 (2 H, m); $^{13}$C NMR (CDCl$_3$), 15.20, 21.26, 29.22, 31.15, 51.79, 52.57, 122.07, 25.11, 126.27, 130.03, 130.53, 137.77, 138.82, 140.29, 141.56, 148.41, 167.14, 171.53.

4-amino-2-(3,5-dimethylphenyl)benzoyl methionine methyl ester 4-nitro-2-(3,5-dimethylphenyl)benzoyl methionine methyl ester (0.11 g, 0.26 mmol) was taken up in ethyl acetate (3.0 ml). To this mixture was added SnCl$_2$.2H$_2$O (0.30 g, 1.30 mmol) and the reaction was heated under nitrogen at reflux for 6 h. The mixture was worked up as described for 4-amino-2-phenylbenzoyl methionine methyl ester in Example 2, to give 0.15 g of a yellow film that was wet with solvent. The material was otherwise pure by NMR and was used without further purification. $^1$H NMR (CDCl$_3$) 1.60–1.70 (1 H, m), 1.80–1.90 (1 H, m), 1.99 (3 H, s), 2.05 (2 H, t, J=7.6 Hz), 2.33 (6 H, s), 3.64 (3 H, s), 3.93 (2 H, br s), 4.61–4.64 (1 H, m), 5.82 (1 H, d, J=7.7 Hz), 6.49 (1 H, d, J=2.3 Hz), 6.62 (1 H, dd, J=8.4 Hz, 2.4 Hz), 6.98 (2 H, s), 7.00 (1 H, s), 7.65 (1 H, d, J=8.3 Hz); $^{13}$C NMR (CDCl$_3$) 15.08, 21.17, 29.28, 31.49, 51.70, 52.18, 113.30, 115.94, 123.55, 126.36, 129.32, 131.23, 138.15, 140.72, 141.92, 148.40, 168.45, 172.01.

N-BOC-S-trityl-cysteine-4-amino-2-(3,5-dimethylphenyl)benzoyl methionine methyl ester 4-amino-2-(3,5-dimethylphenyl)benzoyl methionine methyl ester (0.10 g, 0.26 mmol) was dissolved into dry CH$_2$Cl$_2$ (1.4 ml) and it was allowed to stand. In another flask, N-BOC-S-trityl-Cys (0.12 g, 0.26 mmol) was dissolved into THF (4.4 ml) and was reacted with IBCF (0.03 ml) and Et$_3$N (0.04 ml) as described above. The product was worked up as described for N-BOC-S-trityl-cysteine-4-aminobenzoyl methionine methyl ester in Example 1 and chromatographed on silica gel using a 1:1 hexanes and ethyl acetate elution mixture to give 0.12 g (56.0%) of pure material. $^1$H NMR (CDCl$_3$) 1.33 (9 H, ), 1. 61–1.68 (1 H, m), 1.73–1.91 (4 H, m) , 1.96 (2 H, t, J=7.6 Hz) , 2.24 (6 H, s), 2.57–2.64 (2 H, m), 3.57 (3 H, s), 4.00 (1 H, br s), 4.54–4.58 (1 H, m), 5.84 (1 H, d, J=7.8 Hz), 5.97 (1 H, br d), 6.90 (1 H, s), 6.92 (2 H, s), 7.18–7.22 (9 H, m), 7.27–7.40 (7 H, m), 7.55 (1 H, m), 7.61 (1 H, m), 8.58 (1 H, br s); $^{13}$C NMR (CDCl$_3$) 15.11, 21.20, 27.79, 29.25, 31.28, 51.70, 52.28, 54.08, 60 .32, 71.45, 80.75, 118.01, 120.80, 126.82, 127.98, 129.41, 129.87, 130.22, 138.11, 139.18, 139.79, 141.06, 144.17, 168.38, 169.04, 171.82.

TFACysteine-4-amino-2- (3, 5-dimethylphenyl) benzoyl methionine FTI275

N-BOC-S-trityl-cysteine-4-amino-2-(3,5-dimethylphenyl)benzoyl methionine methyl ester (0.12 g, 0.15 mmol) was placed into THF (0.9 ml) and was reacted with 0.5M of LiOH (0.6 ml) at 0° C. as described above, followed by deprotection with TFA (1. 5 ml) and Et$_3$SiH (0. 24 ml) . Addition of excess scavenger does not appear to affect the result. The product was purified by preparative HPLC to give 23.8 mg (27.3%). mp 135–138° C.; $^1$H NMR (CDCL$_3$) 1.76–1.84 (1 H, m) 2.00–2.17 (6 H, m), 2.33 (6 H, s), 3.05 (1 H, dd, J=14.6 Hz, 7.3 Hz), 3.17 (1 H, dd, J=14.6 Hz, J=4.9 Hz) , 4.15 (1 H, dd, J=7.3, 4.9 Hz), 4.45–4.48 (1 H, m), 7.02 (3 H, s), 7.53 (1 H, d, J=8.0 Hz), 7.66 (2 H, m); $^{13}$C (CD$_3$OD) 14.96, 21.51, 26.28, 30.91, 31.70, 53.03, 56.98, 119.27, 122.30, 127.52, 130.07, 130.57, 133.37, 139.28, 140.39, 141.29, 142.86, 166.89, 172.60, 174.81.

EXAMPLE 7

SYNTHESIS OF FTI-266

4-amino-1-naphthoic acid 4-amino-1-naphthalenecarbonitrile (1.50 g, 8.91 mmol) was dissolved into a 50% KOH solution (18 ml). The heterogeneous solution was heated at reflux for 2–3 days. Once the solution became homogenous and TLC showed no more starting material, the deep red solution was cooled and poured over 200 ml of water. The solution was then filtered and the acid was precipitated with concentrated HCl. The red crystals were filtered and the filtrate was refiltered to give pink crystals. The first fraction was treated with activated carbon to remove some of the red color. 1.51 g (90.6%) of product was obtained. mp 169°–171° C.; $^1$H NMR (CD$_3$OD) 6.69 (1 H, d, J=8.2 Hz), 7.38–7.43 (1 H, m), 7.48–7.54 (1 H, m), 8.03 (1 H, d, J=8.5 Hz), 8.13 (1 H, d, J=8.2 Hz), 9.09 (1 H, d, J=8.5 Hz); $^{13}$C NMR (CD$_3$OD) 107.39, 114.61, 122.99, 123.92, 125.21, 127.40, 128.48, 135.04, 151.35, 171.44; HRMS calc. for C$_{11}$H$_7$NO$_2$, 187.0633; found, 187.0642.

N-BOC-4-amino-1-naphthoic acid 4-amino-1-naphthoic acid (0.86 g, 4.61 mmol) was dissolved into dioxane (9.2 ml) and 0.5M NaOH (9.2 ml). Di-t-butyl dicarbonate (1.11 g, 5.07 mmol) was added and the mixture was stirred overnight. The reaction mixture was worked up as described for N-BOC-4-aminobenzoic acid in Example 1 to give 0.76 g (56.7%) of reddish pink solid. mp 194°–195° C.; $^1$H NMR (CD$_3$OD) 1.56 (9 H, s), 7.53–7.62 (2 H, m), 7.79 (1 H, d, J=8.1 Hz), 8.12 (1 H, d, J=8.0 Hz), 8.22 (1 H, d, J=8.18 Hz), 9.02 (1 H, d, J=8.9 Hz); $^{13}$C NMR (CD$_3$OD), 26.68, 81.62, 119.06, 123.40, 124.57, 127.03, 127.37, 128.49, 128.77, 131.89, 133.76, 139.86, 155.95, 170.73; anal. calc. for C$_{17}$H$_{17}$NO$_4$, C: 66.90, H: 5.96, N: 4.88; found C: 66.49, H: 6.08, N: 4.79; m/z (EI), 289; HRMS calc. for C$_{16}$H$_{17}$NO$_4$, 287.1158; found, 287.1151.

N-BOC-4-amino-1-naphthoyl methionine methyl ester

N-BOC-4-amino-1-naphthoic acid (0.46 g, 1.60 mmol), methionine methyl ester hydrochloride (0.35 g, 1.76 mmol), EDCI (0.43 g, 1.76 mmol), HOBT (0.24 g, 1.76 mmol) and Et$_3$N (0.27 ml) in CH$_2$Cl$_2$ (6.4 ml) were reacted as described for N-BOC-4-aminobenzoyl methionine methyl ester in Example 1. After workup and recrystallization from ethyl acetate and hexanes, 0.44 g (63.6%) of pale pink crystals were obtained. mp 131°–132° C.; $^1$H NMR (CDCl$_3$) 1.57 (9 H, s), 2.11–2.21 (4 H, m), 2.29–2.41 (1 H, m), 2.65 (2 H, t, J=7.1 Hz), 3.83 (3 H, s), 4.99–5.06 (1 H, m), 6.68 (1 H, d, J=8.0), 7.02 (1 H, s), 7.56–7.59 (2 H, m), 7.69 (1 H, d, J=7.9 Hz), 7.87–7.90 (1 H, m), 8.02 (1 H, d, J=7.9 Hz), 8.44–8.48 (1 H, m); $^{13}$C NMR (CDCl$_3$) 15.56, 28.31, 30.19, 31.65, 52.06, 52.64, 81.17, 115.82, 120.18, 125.79, 126.37, 126.53, 127.18, 131.02, 135.65, 152.93, 169.04, 172.40; HRMS calc. for $C_{22}H_{28}N_2O_5S$, 432.1719; found 432.1702; m/z (FAB) 433 (M+1).

HCl.4-amino-1-naphthoyl methionine methyl ester

N-BOC-4-amino-1-naphthoyl methionine methyl ester (0.57 g, 1.31 mmol) was deprotected with HCl/ether to yield 0.31 g (64.1%) of white solid. mp 178°–181° C.; $^1$H NMR (CD$_3$OD) 2.08–2.16 (4 H, m), 2.20–2.30 (1 H, m), 2.57–2.75 (2 H, m), 3.82 (3 H, s), 4.87–4.91 (1 H, m), 7.59 (1 H, d, J=7.5 Hz), 7.67 (1 H, d, J=7.5 Hz), 7.71–7.80 (2 H, m), 8.03 (1 H, dd, J=7.1 Hz, 2.0 Hz), 8.35 (1 H, dd, J=6.8 Hz, 1.8 Hz); $^{13}$C NMR (CD$_3$OD) 15.23, 31.40, 53.01, 53.33, 119.90, 122.20, 126.15, 127.41, 127.77, 129.09, 129.31, 131.50, 132.33, 135.64, 171.77, 173.83; m/z (FAB), 369 (M+1).

N-BOC-S-trityl-cysteine-4-amino-1-naphthoyl methionine methyl ester

N-BOC-S-trityl-Cys (0.31 g, 0.67 mmol) in dry THF (11.2 ml) was reacted with Et$_3$N (0.10 ml) and IBCF (0.10 ml, 0.74 mmol) at –10° C. as described above. HCl.4-amino-1-naphthoyl methionine methyl ester (0.25 g, 0.67 mmol) in dry CH$_2$Cl$_2$ (3.5 ml) was added and the mixture was stirred overnight under nitrogen. The mixture was worked up as described for N-BOC-S-trityl-cysteine-4-aminobenzoyl methionine methyl ester in Example 1, and the crude material was chromatographed on silica gel using a 2:1 mixture of hexanes and ethyl acetate to give 0.20g (37.5 %) of pure product. $^1$H NMR (CDCl$_3$) 1.48 (9 H, s), 2.10–2.20 (4 H, m), 2.30–2.37 (1 H, m), 2.63 (2 H, t, J=7.4), 2.74 (1 H, J=12.9 Hz, J=5.3 Hz), 2.90 (1 H, J=12.9 Hz, 6.2 Hz), 3.81 (3 H, s), 4.96–5.03 (2 H, m), 6.77 (1 H, d, J=8.0 Hz), 7.18–7.33 (11 H, m), 7.44–7.56 (7 H, m), 7.60 (1 H, d, J=7.7 Hz), 7.88 (1 H, d, J=8.0 Hz), 8.00 (1 H, d, J=7.1 Hz), 8.37 (1 H, d, J=8.4 Hz), 8.94 (1 H, br s); $^{13}$C NMR (CDCl$_3$) 15.23, 26.52, 31.41, 31.50, 52.98, 53.31, 56.79, 68.15, 122.52, 123.54, 126.16, 126.99, 128.03, 128.39, 129.52, 132.30, 134.04, 135.24, 168.08, 172.38, 173.94.

TFA cysteine-4-amino-1-naphthoyl methionine, FTI-270

N-BOC-S-trityl-cysteine-4-amino-1-naphthoyl methionine methyl ester (83.3 mg, 0.11 mmol) was taken up in THF (0.7 ml) and to this mixture was added 0.5M LiOH (0.43 ml) at 0° C. The mixture was stirred at 0° C. for 35 minutes. The solvent was removed in vacuo using a cold water bath. The residue was worked up as described for TFA-cysteine-4-amino-3-methylbenzoyl methionine in Example 2, and 74.1 mg of the free acid was obtained. This was then dissolved into CH$_2$Cl$_2$ (1 ml) and Et$_3$SiH (0.015 ml) was added followed by TFA (1 ml). The reaction mixture was stirred at room temperature for 1 h and worked up as further described for TFA-cysteine-4-amino-3-methylbenzoyl methionine in Example 2. After lyophilization, 42.4 mg of crude material was obtained which was then purified on the HPLC using 0.1% TFA in water and acetonitrile. mp 121°–125° C.; $[\alpha]^{25}_D$=+2.4°(c=0.8, H$_2$O); $^1$H NMR (CD$_3$OD) 2.03–2.13 (4 H, m), 2.22–2.36 (1 H, m), 2.59–2.74 (2 H, m), 3.16–3.33 (2 H, m), 4.42 (1 H, m), 4.84–4.89 (1 H, m), 7.57–7.61 (2 H, m), 7.64 (1 H, d, J=7.7 Hz), 7.70 (1 H, d, J=7.7 Hz), 8.08–8.11 (1 H, m), 8.29–8.32 (1 H, m), 8.98 (1 H, d, J=7.7 Hz); $^{13}$C NMR (CD$_3$OD) 15.19, 26.45, 31.50, 31.63, 53.20, 56.72, 122.52, 123.43, 126.43, 126.12, 127.02, 127.96, 128.32, 129.49, 132.27, 134.15, 135.12, 168.11, 172.41, 175.17; anal. calc. for $C_{21}H_{23}F_3N_3O_6S_2$, C: 47.19, H: 4.34, N: 7.86; found, C: 46.53, H: 4.56, N: 7.59; Note: difference for C is 0.65.

HCl.cysteine-4-amino-1-naphthoyl methionine methyl ester FTI-270.HCl

TFA.cysteine-4-amino-1-naphthoyl methionine (0.12 g, 0.15 mmol) was dissolved in CH$_3$OH (4.3 ml). To this solution was added a solution of HgCl$_2$ (0.23 g, 0.86 mmol) in CH$_3$OH (4.3 ml). The procedure was continued as described above and after HCl/Et$_2$O precipitation and several reprecipitations 31.0 mg (18.3%) of pure white material was obtained. mp sub 137° C., decomp 214°–215° C.; $[\alpha]^{25}_D$=–32.0° (c=1CH$_3$OH); $^1$H NMR (CD$_3$OD) 2.12 (3 H, s), 2.21–2.28 (1 H, m), 2.57–2.73 (3 H, m), 3.20–3.34 (2 H, m), 3.82 (3 H, s), 4.39–4.43 (1 H, m), 7.61–7.68 (3H, m), 7.78 (1H, d, J=7.7 Hz), 8.13–8.16 (1H, m), 8.28–8.32 (1 H, m); $^{13}$C (CD$_3$0D) 15.23, 26.52, 31.41, 31.50, 52.98, 53.31, 56.79, 122.52, 123.54, 126.16, 126.99, 128.03, 128.39, 129.52, 132.30, 134.04, 135.24, 168.08, 172.38, 173.94.

EXAMPLE 8

SYNTHESIS OF FTI-254

N-Boc-S-trityl cysteinal

Triethylamine (2.22 mL, 16 mmoL) and N,O-dimethylhydroxylamine hydrochloride (1.57 g, 16.1 mmol) were added to a solution of N-Boc-S- trityl cysteine (7.44 g, 16 mmol) in 85 mL of methylene chloride. This mixture was cooled in an ice bath and 1-(3-dimethylaminopropyl)-3-methylcarbodiimide hydrochloride (EDCI, 3.08 g, 16.0 mmol) and HOBT (2.17 g, 16 mmol) was added. The mixture was stirred at 0° C. for 1 hr and at room temperature for a further 10 hr. The mixture was extracted with methylene chloride and 0.5 N HCl. The organic layer was washed consecutively with 0.5N HCl, concentrated NaHCO$_3$ and brine. The organic layer was dried and evaporated. The residue was purified by flash column chromatography (1.5 : 1=hexane : ethylacetate) to give a white foam (7.40 g, 91%). m.p. 59°–60 ° C. (decomp) . $^1$H NMR (CDCl$_3$) δ7.41 (m, 6H) , 7.20–7.31 (m, 9H), 5.13 (d, 8.9 Hz, 1H), 4.76 (br s, 1H), 3.64 (s, 3H), 3.15 (s, 3H), 2.56 (dd, 4.7 and 12.1 Hz, 1H), 2.39 (dd, 7.8 and 12.1 Hz, 1H), 1.43 (s, 9H). $^{13}$C NMR (CDCl$_3$) δ170.7, 154.9, 144.2, 129.3, 127.6, 126.4, 79.3, 66.4, 61.2, 49.5, 33.8, 31.8, 28.1. This carboxyamide (2.02 g, 4.0 mmol) was dissolved in 30 mL of ether and cooled to –10° C. Lithium aluminum hydride (167 mg, 4.40 mmol) was added and the mixture was stirred for 15 min under the nitrogen. Then 40 mL of 0.5N HCl was added and the solution was extracted with ether. The ether layer was washed with 0.5N HCl and dried. The evaporation of solvents gave a white foam (1.80 g) which was used for further reaction without purification. The $^1$H NMR spectrum of this compound was complex. The percentage of the aldehyde was about 65–70%, which was calculated according to the integration of the sharp singlet (δ9.17) and the trityl peak (δ7.40, m, 6H; 7.28, m, 9H). Lowering the temperature to –45° C. did not improve the aldehyde percentage.

4-N-[2(R)-tert-Butoxycarbonylamino-3-triphenylmethylthiopropyl]aminobenzoyl methionine methyl ester.

One equivalent of N-Boc-S-trityl cysteinal in 10 mL of methanol was added to a solution of 4-aminobenzoyl methionine methyl ester hydrochloride (1.7836 g, 5.6 mmol) in 60 mL of methanol and 4 mL of glacial acetic acid. Sodium cyanoboronhydride (0.528 g, 8.40 mmol) was added to this deep colored solution at 0° C. The mixture was stirred at room temperature for 15 hr. After the evaporation of solvents, the residue was extracted with ethyl acetate and concentrated sodium bicarbonate. The organic phase was dried and the solvents were evaporated. The residue was purified through flash column chromatography (ethyl acetate/hexane =1:1) to give a pure desired product (2.52 g, 65%). $^1$H NMR (CDCl$_3$) δ7.63 (d, 8.6 Hz, 2H), 7.43 (m, 6H), 7.21–7.32 (m, 9H), 6.73 (d, 7.6 Hz, 1H, Met amide), 6.50 (d, 8.6 Hz, 2H), 4.91 (ddd, 5.1 Hz, 5.3 Hz and 7.6 Hz, 1H, Met α H), 4.59 (d, 8.9 Hz, 1 H, Boc amide), 4.25– 4.40 (br, 1H, NHPh), 3.80 (m, 1 H, Cys α H), 3.78 (s, 3 H, OCH$_3$), 3.09 (d, 6.3 Hz, 2 H, CH$_2$NH), 2.55–2.60 (m, 2H, CH$_2$SCPh$_3$), 2.46 (d, 5.0 Hz, 2 H, CH$_2$SCH$_3$), 2.23–2.28 (m, 1H, Met CH$_2$), 2.07–2.12 (m, 1H, Met CH$_2$), 2.09 (s, 3 H, SCH$_3$), 1.43 (s, 9 H, Boc).

4-N-[2(R)-Amino-3-mercaptopropyl]aminobenzoyl methionine methyl ester.

The fully protected 4-N-[2(R)-tert-Butoxycarbonylamino-3triphenylmethylthiopropyl]amino-benzoyl methionine methyl ester (1.31 g, 1.83 mmol) was dissolved into 20 mL of methanol. To this solution was added mercuric chloride (1.09 g, 4.04 mmol) in 5 mL of methanol. The mixture was refluxed for 20 min and then cooled down. The clear solution was removed and the solid precipitate was washed with 5 mL of methanol. The solid was dried and then suspended in 15 mL of methanol. The suspension was stirred and reacted with hydrogen sulfide gas for 1 hr. The black precipitate was removed by centrifugation. The clear solution was evaporated to dryness. The residue was dissolved in 6 mL of methylene chloride followed by the addition of 20 mL of 3N HCl in ether. The white precipitate was filtered and dried to give a hydrochloride salt of the desired product (0.60 g, 73%). $^1$H NMR (CD$_3$OD) δ7.73 (d, 8.8 Hz, 2H), 6.75 (d, 8.8 Hz, 2H), 4.74 (dd, 4.9 Hz and 4.3 Hz, 1H, Met α H), 3.72 (s, 3 H, OCH$_3$), 3.43–3.59 (m, 3H, CH$_2$NH and Cys α H), 2.93 (dd, 3.9 Hz and 14.4 Hz, 1 H, CH$_2$SH) , 2.81 (dd, 5.2 Hz and 14.5 Hz, 1H, CH$_2$SH), 2.49–2.66 (m, 2H, CH$_2$SCH$_3$) , 2.07–2.20 (m, 2H, Met CH$_2$), 2.10 S, 3H, sCH$_3$)

4-N-[2(R)-Amino-3-mercaptopropyl] laminobenzoyl methionine

The fully protected peptide 4-N-[2(R) -tert-Butoxycarbonylamino-3- triphenylmethylthiopropyl]-aminobenzoyl methionine methyl ester (567 mg, 0.79 mmol) was dissolved into 3.0 mL of 0.5N lithium hydroxide and 3.0 mL of tetrahydrofuran. The mixture was stirred at 0° C for 1 hr. After the evaporation of solvents, the residue was dissolved in water and extracted with methylene chloride and iN hydrochloric acid. The organic phase was dried and the solvents were evaporated. The residue was dissolved in a mixture of lmL of methylene chloride and 2 mL of trifluoroacetic acid. Triethylsilane was added dropwise until the deep brown color disappeared. The mixture was kept at rt for 1 hr. The solvents were evaporated and the residue was dried. This residue was dissolved in 1 mL of 1.7N HCl in acetic acid followed by the addition of 20 mL of 3N HCl in ether. The white precipitate was filtered and dried to give a hydrochloride salt of the desired product (159 mg, 46%). Analytical HPLC showed purity over 98%. $^1$H NMR (CD$_3$OD) 6 7.74 (d, 8.7 Hz, 2H), 6.75 (d, 8.7 Hz, 2H), 4.73 (dd, 4.5 Hz and 4.7 Hz, 1H, Met α H), 3.45–3.58 (m, 3 H, CH$_2$NH and Cys a H), 2.93 (dd, 4.5 Hz and 14.6 Hz, 1 H, CH$_2$SH), 2.80 (dd, 5.3 Hz and 14.6 Hz, 1H, CH$_2$SH), 2.53–2.64 (m, 2H, CH$_2$SCH$_3$), 2.15–2.23 (m, 1 H, Met CH$_2$), 2.07–2.13 (m, 1 H Met CH$_2$), 2.10 (s, 3 H, SCH$_3$)

EXAMPLE 9

Synthesis of FTI-284

4-Nitro-2-phenylbenzoyl-[1'(S)-methoxycarbonyl-3'-methylsulfonyl]propyl amide 4-nitro-2-phenylbenzoyl methionine methyl ester (525 mg, 1.28 mmol), N-methylmorpholine oxide (453 mg, 3.87 mmol) and 0.5 mL of osmium tetroxide (2.5 wt. % solution in tert-butanol) were added to a mixture of 40 mL of acetone and 10 mL of water. The mixture was stirred at rt overnight. After the addition of excess sodium sulfite, the reaction mixture was extracted with ethyl acetate and washed with concentrated sodium bicarbonate. The organic phase was dried and the solvents were evaporated to give a solid (570 mg, 100%). $^1$H NMR (CDCl$_3$) δ8.29 (d, 7.7 Hz, 1H), 8.25 (s, 1H), 7.83 (d, 7.7 Hz, 1H), 7.43–7.55 (m, 5H), 6.15 (d, 7.3 Hz, 1H, Met amide), 4.68 (ddd, 5.0 Hz, 5.1 Hz and 7.3 Hz, 1H, Met α H), 3.70 (s, 3 H, OCH$_3$) , 2.85 (s, 3 H, SCH$_3$) 2.69–2.81 (m, 1H, CH$_2$SO$_2$), 2.58–2.66 (m, 1H, CH$_2$SO$_2$), 2.21–2.33 (m, 1H, Met CH$_2$), 1.96–2.08 (m, 1H, Met CH$_2$)

4-N-[2(R)-tert-Butoxycarbonylamino-3-triphenylmethylthiopropyl]amino-2-phenylbenzoyl-[1'(S)-methoxycarbonyl-3'-methylsulfonyl]propyl amide The 4-Nitro-2-phenylbenzoyl-[1'(S)- methoxycarbonyl-3'-methylsulfonyl]propyl amide (430 mg, 1.02 mmol) was dissolved in 20 mL of methanol. A catalytic amount of 5% palladium on carbon was added and the mixture was hydrogenated at 40 PSI for 1.5 hr. The mixture was filtered and the filtrate was evaporated to dryness to give 4-amino product (400 mg, 100%). $^1$H NMR (CD$_3$OD) δ7.70 (d, 8.0 Hz, 1H), 7.38–7.47 (m, 7H), 4.53 (dd, 4.6 Hz and 4.8 Hz, 1H, Met α H), 3.72 (s, 3 H, OCH$_3$), 2.89 (s, 3 H, S0$_2$CH$_3$), 2.79–2.85 (m, 1 H, CH$_2$SO$_2$), 2.58–2.68 (m, 1H, CH$_2$SO$_2$), 2.19–2.29 (m, 1 H, Met CH$_2$), 1.93–2.04 (m, 1 H, Met CH$_2$). This amine was dissolved in 15 mL of methanol and 0.8 mL of acetic acid. One equivalent of N-Boc-S-trityl cysteinal was added followed by the addition of sodium cyanoboronhydride (97 mg, 1.5 eq). The mixture was stirred at rt overnight. After the evaporation of solvents, the residue was extracted with ethyl acetate and concentrated sodium bicarbonate. The organic phase was dried and solvents were evaporated. The residue was purified through flash column chromatography (ethyl acetate/hexane/methanol =15:15:2) to give a pure product (500 mg, 60%). $^1$H NMR (CDCl$_3$) δ7.64 (d, 8.5 Hz, 1H), 7.37–7.46 (m, 11H), 7.18–7.33(m, 9H), 6.53 (d, 8.5 Hz, 1H), 6.34 (s, 1H), 5.74 (d, 7.5 Hz, 1 H, Met amide), 4.64 (ddd, 4.9 Hz, 5.1 Hz and 7.5 Hz, 1 H, Met a H), 4.55 (d, 7.5 Hz, 1 H, Boc amide), 4.26 (br, 1 H, NHPh), 3.79 (m, 1 H, Cys α H), 3.68 (s, 3H, OCH$_3$), 3.10 (t, 5.7 Hz, 2 H, CH$_2$NHPh), 2.84 (s, 3 H, SO$_2$CH$_3$), 2.62–2.82 (m, 2 H, CH$_2$SO$_2$), 2.45 (d, 2 H, CH$_2$SCPh$_3$), 2.19–2.27 (m, 1 H, Met CH$_2$), 1.84–1.95 (m, 1H, Met CH$_2$), 1.41 (s, 9H).

4-N-[2(R)-Amino-3-mercaptopropyl]amino-2-phenylbenzoyl-[1'(S)-methoxycarbonyl-3'-methylsulfonul]propyl amide, FTI-284

The fully protected peptide 4-N-[2(R) -tert-Butoxycarbonylamino-3-triphenylmethyl-thiopropyl] amino-2-phenylbenzoyl-[1'(S)-methoxycarbonyl-3'-methylsulfonyl]propyl amide(277 mg, 0.33 mmol) was dissolved into 5 mL of methanol. To this solution was added mercuric chloride (229 mg, 2.50 eq) in 2 mL of methanol. The mixture was refluxed for 20 min. The precipitate was dried and then suspended in 10 mL of methanol. This mixture was reacted with hydrogen sulfide gas. The reaction mixture was centrifuged and the clear solution was evaporated. The residue was dissolved in 2 mL of methylene chloride followed by the addition of 20 mL of 3N HCl in ether. The white precipitate was collected and dried to give a hydrochloride salt of the desired product (165 mg, 89%). $^1$H NMR (CD$_3$OD) δ7.44 (d, 8.4 Hz, 1H), 7.32–7.40 (m, 5H), 6.77 (d, 8.4 Hz, 1H), 6.68 (s, 1H), 4.45 (dd, 4.5 Hz and 4.7 Hz, 1 H, Met α H), 3.69 (s, 3 H, OCH$_3$), 3.40–3.57 (m, 3 H, CH$_2$NHPh and Cys a H), 2.78–2.96 (m, 3 H, CH$_2$SH and CH$_2$SO$_2$), 2.89 (S, 3 H, SO$_2$CH$_3$), 2.60–2.69 (m, 1 H, CH$_2$SO$_2$), 2.15–2.24 (m, 1 H, Met CH$_2$), 1.91–2.02 (m, 1 H, Met CH$_2$).

EXAMPLE 10

SYNTHESIS OF FTI-277

4-N-[2(R)-tert-Butoxycarbonyl-3-triphenylmethylthiopropyl]amino-2-phenylbenzoyl methionine methyl ester The coupling of 4-amino-2-phenylbenzoyl methionine methyl ester (3.88 g, 10 mmol) with one equivalent of N-Boc-S-trityl cysteinal in the presence of 1.5 equivalent of sodium cyanoboronhydride gave a crude mixture which was purified through flash column chromatography (ethyl acetate/hexane =1:1) to give a pure desired product (5.83 g, 74%). $^1$H NMR (CDCl$_3$) δ 7.65 (d, 8.5 Hz, 1H), 7.32–7.45 (m, 11H), 7.18–7.30 (m, 9H), 6.50 (d, 8.5 Hz, 1H), 6.33 (s, 1H), 5.65 (d, 7.6 Hz, 1 H, Met amide), 4.62 (ddd, 5.0 Hz, 5.2 Hz and 7.6 Hz, 1 H, Met α H), 4.54 (d, 8.1 Hz, Boc amide), 4.18 (br, 1 H, NHPh), 3.78 (m, 1 H, Cys α H), 3.64 (s, 3 H, OCH$_3$), 3.10 (t, 6.1 Hz, 2 H, CH$_2$NHPh), 2.45 (d, 5.0 Hz, 2 H, CH$_2$SCPh$_3$), 2.04–2.10 (m, 2 H, CH$_2$SCH$_3$), 2.00 (s, 3 H, SCH$_3$), 1.81–1.92 (m, 1 H, Met CH$_2$), 1.61–1.70 (m, 1 H, Met CH$_2$), 1.40 (s, 9H). $^{13}$C NMR (CDCl$_3$) δ172.0, 168.3, 155.7, 149.4, 144.3, 141.6, 141.1, 131.3, 129.5, 128.7, 128.5, 127.9, 127.7, 126.8, 122.6, 113.6, 111.3, 79.8, 67.1, 52.2, 51.7, 49.5, 47.2, 34.3, 31.6, 29.4, 28.3, 15.2.

4-N-[2(R)-Amino-3-mercaptopropyl]amino-2-phenylbenzoyl methionine methyl ester, FTI-277.

The fully protected peptide 4-N-[2(R)-tert-Butoxycarbonyl-3-triphenylmethyl-thiopropyl]amino-2-phenylbenzoyl methionine methyl ester(1.57 g, 2.0 mmol) was first reacted with mercuric chloride (1.36 g, 5.0 mmol) and then reacted with hydrogen sulfide gas in methanol to give a hydrochloride salt of the desired product (0.808 g, 84%). Analytical HPLC showed purity over 98%. $[α]^{25}_D$= −12.1° (c=0.008, CH$_3$OH). $^1$H NMR (CD$_3$OD) δ7.42 (d, 8.3 Hz, 1H), 7.30–7.38 (m, 5H), 6.78 (d, 8.3 Hz, 1H), 6.71 (s, 1H), 4.47 (dd, 4.2 Hz and 5.1 Hz, 1 H, Met α H), 3.68 (s, 3 H, OCH$_3$), 3.44–3.54 (m, 3 H, CH$_2$NHPh and Cys a H), 2.94 (dd, 4.1 Hz and 14.6 Hz, 1 H, CH$_2$SH), 2.81 (dd, 5.0 Hz and 14.6 Hz, 1 H, CH$_2$SH), 2.12–2.22 (m, 1 H, CH$_2$SCH$_3$), 2.03–2.10 (m, 1 H, CH$_2$SCH$_3$), 2.00 (s, 3 H, SCH$_3$), 1.90–1.97 (m, 1 H, Met CH$_2$), 1.73–1.82 (m, 1 H, Met CH$_2$). $^{13}$C NMR (CD$_3$OD) δ173.7, 173.4, 150.7, 143.5, 142.3, 131.2, 129.8, 129.5, 128.6, 125.6, 115.6, 112.2, 53.7, 53.2, 52.8, 45.0, 31.3, 30.8, 25.3, 15.0.

EXAMPLE 11

SYNTHESIS OF FTI-276

4-N-[2(R)-Amino-3-mercaptopropyl] amino-2-phenylbenzoyl methionine

The fully protected peptide 4-N-[2(R)-tert-Butoxycarbonyl-3-triphenylmethylthiopropyl]-amino-2-phenylbenzoyl methionine methyl ester (2.36 g, 3 mmol) was first reacted with lithium hydroxide and then with trifluoroacetic acid to give a crude product (1.30 g, 77% yield, 85% purity shown by HPLC) which was further purified through preparative HPLC to give a pure product (0.98 g, 75%). $[α]^{25}_D$=−13.6° (c=0.005, CH$_3$OH). $^1$H NMR (CD$_3$OD) δ 7.44 (d, 8.4 Hz, 1H), 7.30–7.41 (m, 5H), 6.75 (d, 8.4 Hz, 1H), 6.68 (s, 1H), 4.43 (dd, 4.2 Hz and 5.1 Hz, 1H, Met α H), 3.44–3.58 (m, 3 H, CH$_2$NHPh and Cys α H), 2.95 (dd, 4.4 Hz and 14.5 Hz, 1 H, CH$_2$SH), 2.83 (dd, 5.0 Hz and 14.5 Hz, 1H, CH$_2$SH), 2.14–2.23 (m, 1H, CH$_2$SCH$_3$), 2.05–2.11 (m, 1 H, CH$_2$SCH$_3$), 2.00 (s, 3 H, SCH$_3$), 1.91–1.99 (m, 1H, Met CH$_2$), 1.72–1.81 (m, 1 H, Met CH2). $^{13}$C NMR (CD$_3$OD) δ 176.4, 173.5, 150.4, 143.0, 141.5, 131.0, 129.7, 129.4, 128.9, 124.6, 115.0, 112.2, 53.3, 44.4, 30.8, 30.1, 24.9, 14.8.

Other compounds of the invention (in particular those of claims 14–18) are synthesizable by modifications of the procedure described for the 2-phenyl-4-aminobenzoic acid derivative of claim 3. In particular, modifications of the Suzuki couping method will allow the incorporation of an alkoxy-, chloro, bromo or methyl substituted phenyl group onto the 4-aminobenzoic acid spacer. As with the unsubstituted derivative, 4-nitro-2-bromotoluene will be coupled with the corresponding substituted phenyl boronic acid derivative (alkoxyphenyl or chloro-, bromo- or methylphenylboronic acid) under paladium catalyzed conditions. The appropriately substituted 2-(substituted) phenyl-4-nitro toluene derivative will be incorporated into the peptidomimetic synthesis as described for the 2- phenyl case.

In a similar way the precursor to the 2-naphthyl-, 2-thiophene-, 2-pyrrole-, and 2-pyridyl-4-aminobenzoic acid spacers can be prepared by reaction of 4-nitro-2-bromotoluene with naphthalene-2-boronic acid, thiophene-2-boronic acid, pyrrole-2-boronic acid, pyridine- 2,3- or 4-boronic acid.

EXAMPLE 12

FTASE AND GGTASE I ACTIVITY ASSAY

FTase and GGTase I activities from 60,000×g supernatants of human Burkitt lymphoma (Daudi) cells (ATCC, Rockville, MD) were assayed as described previously for FTase (41). Briefly, 100 μg of the supernatant was incubated in 50 mM Tris, pH 7.5, 50 μM ZnCl$_2$, 20 mM KCl and 1 mM dithiothreitol (DTT). The reaction was incubated at 30° C. for 30 min with recombinant Ha-Ras-CVLS (11 μM) and [3H]FPP (625 nM; 16.3 Ci/mmol) for FTase, and recombinant Ha-Ras-CVLL (5 μand [$^3$H] geranylgeranylpyrophosphate (525 nM; 19.0 Ci/mmol) for GGTase I. The peptidomimetics were mixed with FTase and GGTase before adding to the reaction mixture.

EXAMPLE 13

RAS AND RAPLA PROCESSING ASSAY

H-RasF cells (45) were seeded on day 0 in 100 mm Dishes (costar) in Dulbecco's modified Eagles medium (GIBCO) and allowed to grow to 40–60% confluency. On days 1 and 2, cells were fed with 4 ml of medium per plate plus various concentrations of FTI-277 or vehicle. On day 3, cells were washed one time with ice cold PBS and were collected and lysed by incubation for 30–60 min on ice in lysis buffer (41). Lysates were cleared (14,000 rpm, 4° C., 15 min) and supernatants collected. Equal amounts of lysate were separated on a 12.5% SDS-PAGE, transfered to nitrocellulose, and a western blot performed using a anti-Ras antibody (Y13–238, ATCC) or anti-RaplA antibody (Santa Cruz Biotechnology, Santa Cruz, Calif.). Antibody reactions were visualized using peroxidase-conjugated goat anti-rat IgG for Y13–238 and peroxidase-conjugated goat anti-rabbit IgG for RaplA and an enhanced chemiluminescence detection system (ECL; Amersham Corp.)

EXAMPLE 14

CO-IMMUNOPRECIPITATION OF RAF AND RAS

Cells were seeded on day 0 in 100 mm dishes in 10 ml Dulbecco's Modified Eagles Medium (GIBCO) supplemented with 10% calf serum (Hyclone) and 1% pen/strep (GIBCO). On days 1 and 2 cells were treated with FTI-277 (5 $\mu$M) or vehicle (confluency of cells 40–60%). On day 3, cells were collected by centrifugation in ice cold PBS. Cell pellets were then resuspended in ice cold hypotonic buffer (10 mM Tris, pH 7.5, 5 mM $MgCl_2$, 1 mM DTT, 1 mM PMSF) and cells were sonicated to break up cell pellet to promote separation of cytosol and membrane. The cell suspension was then centrifuged at 2,000 rpm for 10 min to clear debris after which the supernatant was loaded in ultrocentrifuge tubes and spun for 30 min at 100,000×g to SW Ti55 Rotor to separate membrane and cytosol fractions. The cytosol and membrane fractions were lysed on ice for 60 min in buffer containing 30 mM HEPES, pH 7.5, 1% TX-100, 10% glycerol, 10 mM NaCl, 5 mM MgCl2, 2 mM $Na_3VO_4$, 25 mM NaF, 1 mM EGTA, 10 $\mu$M soybean trypsin inhibitor, 25 $\mu$g/ml leupeptin, 10 $\mu$g/ml aprotinin, 2 mM PMSF). The lysates were clarified by centrifugation. Equal amounts of cytosol and membrane fractions were immunoprecipitated using 50 $\mu$l of a 25% Protein-A Sepharose Cl-4B suspension (Sigma) with 1 $\mu$f/ml anti-c-Raf-1 (SC133, Santa Cruz Biotechnology, Santa Cruz, Calif.). The samples were tumbled at 4° C. for 60 min and then washed 5 times in 50 mM HEPES, pH 7.5, 100 mM NaCl, 5 mM $MgCl_2$, 0.1% TX-100, 10% glycerol, 20 mM NaF. The final pellets were run on 12.5% SDS-PAGE, transferred to nitrocellulose, and immunoblotted for the presence of Ras using anti-Ras antibody (Y13–238) and immunoblotted for the presence of Raf (c-Raf-1, SC133, Santa Cruz Biotechnology, Santa Cruz, Calif.). Detection was the same as above for Ras and RaplA processing.

EXAMPLE 15

DETECTION OF GTP AND GDP BOUND TO RAS (FTI-277)

H-RasF cells were seeded and treated as above for Ras/Raf interaction and Ras and RaplA processing. On day 2, however, cells were labeled overnight with [$^{32}$P] orthophosphate at 100 $\mu$Ci/mo (Amersham PBS13) in 10 ml DMEM-phosphate supplemented with 10% calf serum, 1 mg/ml BSA and 20 mM HEPES, pH 7.5. On day 3, the medium was removed and cells were washed one time in ice-cold PBS, scraped from the plate with a cell scraper, collected and centrifuged. The cell pellet was resuspended in ice-cold hypotonic buffer listed above and the cytosol and membrane fractions were separated according to the above description for Ra/Raf association. The cytosol and membrane fractions were lysed on ice for 60 min in 50 mM Tris, pH 7.5, 5 mM $MgCl_2$, 1% Triton X-100 (TX-100), 0.5% DOC, 0.05% SDS, 500 mM NaCl, 1 mM EGTA, 10 $\mu$g/ml aprotinin, 10 $\mu$g/ml soybean trypsin inhibitor, 25 $\mu$g/ml leupeptin, 1 mM DTT, 1 mg/ml BSA. Lysates were cleared and equal amounts of protein were immunoprecipitated using anti-Ras antibody (Y13–259) along with 30 $\mu$l Protein A-Agarose goat anti-rat IgG complex (Oncogene Science) for 60 min at 4° C. Immunoprecipitates were washed 6 times in 50 mM HEPES, pH 7.5, 0.5M NaCl, 0.1% TX-100, 0.0005 SDS, 5 mM $MgCl_2$, drained using a syringe and bound nucleotide eluted in 12 $\mu$l of 5 mM DTT, 5 mM EDTA, 0.2% SDS, 0.5 mM GDP and 0.5 mM GTP at 68° C for 20 min. Immune complexes were spun down quickly and 6 $\mu$l of the supernatent was loaded onto PEI cellulose thin layer chromatography plates (20 cm ×20 cm). Nucleotides were separated by chromatography in 78 g/linter ammonium formate, 9.6% (v/v) concentrated HCl. Plates were analyzed by autoradiogram.

EXAMPLE 16

ANALYSIS OF RAF-I KINASE ACTIVITY

Raf-1kinase was assayed by determining the ability of Raf to transfer phosphate from [$\gamma$-$^{32}$P] ATP to a 19-mer peptide containing an autophosphorylation site. Membrane and cytosol fraction isolation and Raf immunoprecipitates were wshed three times with cold HEPES buffer and twice with kinase buffer (50 mM Tris, pH 7.5, 150 mM NaCl, 12 mM $MnCl_2$ 1 mM DTT, 0.2% Tween 20. Immune complex kinase assays were performed by incubating immunoprecipitaes from membrane and cytosol fractions in 96 $\mu$l of kinase buffer with 20 $\mu$Ci of [$\gamma^{32}$P] ATP (10 mCi/ml, Amersham) and 2 $\mu$l of the Raf-1 substrate peptide (1 mg/ml, Promega) for 30 min at 25° C. The sequence of the Raf-1 substrate peptide is IVQQFGFQRRASDDGKLTD. The phosphorylation reaction was terminated by spotting 50 $\mu$l aliquots of the assay mixture onto Whatman P81 for 40 min in 0.5% orthophosphoric acid and air dried. The amount of 32p incorporated was determined by liquid scintillation counting.

EXAMPLE 17

INHIBITION OF FTASE BY FTI-276 AND OTHER COMPOUNDS

Figure 1B:
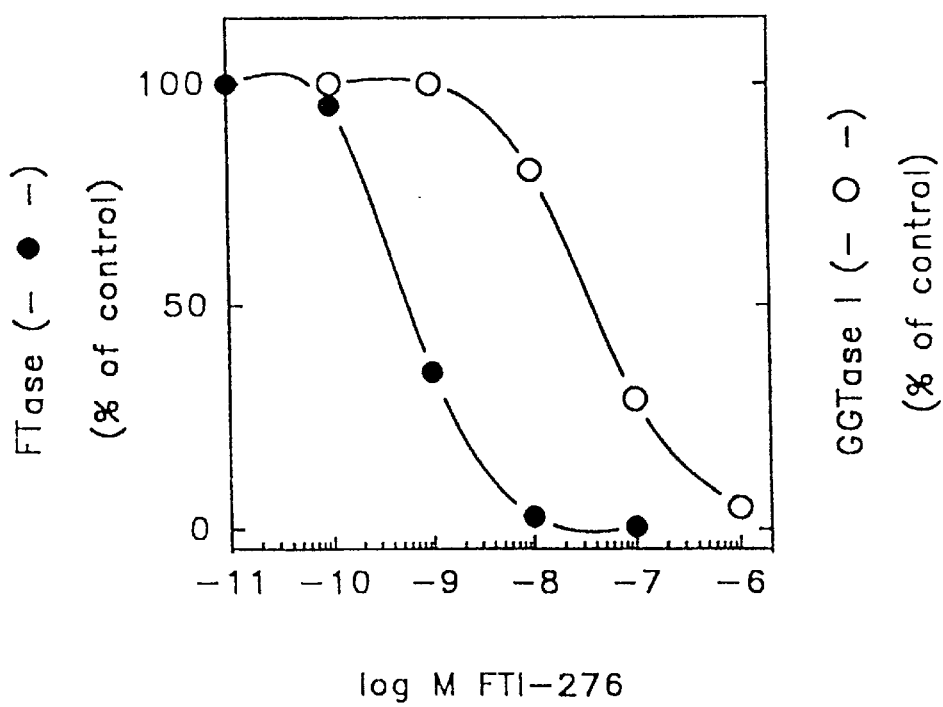

FIG. 1B shows that FTI-276 inhibited the transfer of farnesyl from [$^3$H]FPP to recombinant H-Ras-CVLS with an $IC_{50}$ of 500 pM. FTI-249, the parent compound of FTI-276, inhibited FTase with an $IC_{50}$ of 200,000 pM. Thus, a phenyl ring at the 2 position of the benzoic acid spacer increased inhibition potency of FTase by 400 fold confirming our prediction of a significant hydrophobic pocket within the CAAX binding site of FTase. This extremely potent inhibitor was also highly selective (100-fold) for FTase over the closely related GGTase I (FIG. 1B). FTI-276 inhibited the transfer of geranylgeranyl from [$^3$H]GG-PP to recombinant H-Ras-CVll with an $IC_{50}$ of 50 nM (FIG. 1B). This 100-fold selectivity is superior to the 15-fold selectivity of the parent compound, FTI-249. Data for a number of other compounds of interest are shown in Table 1.

TABLE 1

| Compound | | FTase $IC_{50}$ [nm] | GGTase I $IC_{50}$ [nm] | GG/F |
|---|---|---|---|---|
| FTI | | | | |
| 232 | CABAM | 213 | 1200 | 6 |
| 260 | 3-Me-CABAM | 825 | 9000 | 11 |

TABLE 1-continued

| Compound | | FTase IC$_{50}$ [nm] | GGTase I IC$_{50}$ [nm] | GG/F |
|---|---|---|---|---|
| 261 | 3-OMe-CABAM | 2550 | 50000 | 20 |
| 270 | CANAM | 143 | 3150 | 22 |
| 272 | 2-Ph-CABAM | 5 | 267 | 53 |
| 274 | 2-Ph-CABAM-OMe | 2050 | 30000 | 15 |
| 275 | 2-Xy-CABAM | 405 | 400 | 1 |
| 249 | red.CABAM | 272 | 3967 | 15 |
| 254 | red.CABAM-OMe | 1000 | 19000 | 19 |
| 276 | red.2-Ph-CABAM | 0.5 | 57 | 114 |
| 277 | red.2-Ph-CABAM-OMe | 50 | 1600 | 32 |

EXAMPLE 18

INHIBITION OF RAS PROCESSING BY FTI-277

To facilitate cellular uptake, FTI-277, the methylester of FTI-276, was used in experiments to measure inhibition of Ras processing. H-RasF cells (NIH 3T3 cells transformed with oncogenic (61 leucine) H-Ras-CVLS (45) were treated with FTI-277 (0–50 μM) and the lysates blotted with anti-Ras or anti-Rap1A antibodies. As shown in FIG. 2A, concentrations as low as 10 nN inhibited Ras processing but concentrations as high as 10 μM did not inhbit processing of the geranylgeranylated Rap1A. FTI-277 inhibited Ras processing with an IC$_{50}$ of 100 nM. In contrast, the IC$_{50}$ of FTI-249 is 100 μM, and the most potent CAAX peptidomimetics previously reported inhibited Ras processing at concentrations of 10 μM or higher (44).

The selectivity of FTI-277 for farnesylation but not geranylgeranylation processing is further demonstrated in FIG. 2B. H-RasGG cells (NIH 3T3 cells transformed with oncogenic (61 leucine) H-Ras-CVLL (45) were treated with FTI-277. Processing of RasGG was not affected, whereas that of RasF was completely blocked. The processing of endogenous Ras is also blocked in pZIPneo cells (NIH 3T3 cells transfected with the same plasmid as H-RasF and H Ras FF except the vector contained no oncogenic Ras sequences) and Raf cells (NIH 3T3 cells transformed by an activated viral Raf (48)).

MECHANISM OF DISRUPTION OF RAS ONCOGENIC SIGNALLING BV FTI-277

Ras relays biological information from tyrosine kinase receptors to the nucleus by activation of a cacade of MAPKs (reviewed in 29–31). Upon growth factor stimulation, Ras becomes GTP bound and is then able to recruit the ser/thr kinase c-Raf-1 to the plasma membrane where it is activated. c-Raf-1 then phosphorylates and activates MEK, a dual thr/tyr kinase, which activates MAPK. Recently, epidermal growth factor has been shown to induce association of Raf with Ras (46).

In order to determine the mechanism by which FTI-277 disrupts Ras oncogenic signaling, we transfected NIH 3T3 cells with activated (GTP-locked) Ras and investigated the effects of FTI-277 on the interaction of Ras with its immediate effector, Raf. Various NIH 3T3 cell transfectants (pZIPneo, H-RasF, and H-RasGG) were treated with vehicle or FTI-277, membrane and cytosolic fractions were isolated and immunoprecipitated with anti-Raf antibody as described above. Raf did not associate with Ras in pZIPneo cells which did not contain GTP-locked Ras, as shown in FIG. 3. In contrast, H-RasF and H-RasGG cells contain Ras/Raf complexes in the membrane, but not in the cytosolic fractions, as shown in FIG. 3. Treatment of these cells with FTI-277 resulted in the accumulation of Ras/Raf complexes in the cytosolic but not membrane fractions of H-RasF cells, but not in the H-RasGG cells (FIG. 3). Thus, the disruption of Ras/Raf interaction at the cell membrane and accumulation of these complexes in the cytoplasm occurred only in Ras-F but not Ras-GG cells, in agreement with the Ras processing selectivity results of FIG. 2. Thus, these results demonstrate that inhibition with FTI-277 results in the accumulation of non-farnesylated cytosolic Ras that is capable of binding to Raf. The fact that non-processed Ras can associate with Raf in a non-membranous cytoplasmic environment was confirmed by transfecting NIH 3T3 cells with a GTP-locked Ras that lacks a farnesylated site and, therefore, remains in the cytoplasm (Ras mutant with a 61 leucine oncogenic mutation and a 186 serine mutation) and showing that these cells contained only cytoplasmic Ras/Raf complexes when immunoprecipitated with Raf and blotted with antiRas antibodies (FIG. 3). In short, farnesylation is not required for Ras to bind to Raf.

EXAMPLE 19

DETERMINATION OF NUCLEOTIDE STATE OF RAS

The fact that Raf binds Ras-GTP with much higher affinity than Ras-GDP was used to determine the nucleotide state of Ras in the cytoplasmic Ras/Raf complexes, as described above. In Ras-F cells, only membrane fractions contained GTP-locked Ras, as shown in FIG. 4A. Upon treatment with FTI-277, however, the non-farnesylated cytosolic Ras was found to be GTP bound. Thus, binding of GTP to 61 leucine Ras does not require Ras processing and subsequent plasma membrane association. The ser/thr kinase activity of Raf in Ras/Raf complexes was then determined by immunoprecipitating Raf and assaying for its ability to phosphorylate a 19-mer autophosphorylated peptide. FIG. 4B shows that oncogenic Ras-F induced activation of Raf in the plasma membrane and that treatment with FTI-277 suppressed this activation. More importantly, the cytoplasmic Ras/Raf complexes that were induced by FTI-277 (FIG. 3) had basal levels of Raf kinase activity that were comparable to those of the parental NIH 3T3 cell line pZIPneo (FIG. 4B). Taken together, FIGS. 3 and 4 demonstrate that oncogenic transformation with GTP-locked Ras results in the constitutive recruitment to the plasma membrane and subsequent activation of Raf. Furthermore, FTase inhibition by FTI-277 suppresses this activation by inducing the accumulation of Ras/Raf complexes in the cytoplasm where Ras is GTP-bound but Raf kinase is not activated. The fact that Raf kinase is not activated when bound to Ras in a non-membranous environment is consistent with recent reports that indicate that Raf activation requires an as yet to be determined activating factor at the plasma membrane (47).

We then investigated the effects of FTI-277 on oncogenic Ras activation of MAPK, a Raf downstream signalling event (29–31). Oncogenic activation of MAPK can be easily detected since activated MAPK migrates slower in SDS-PAGE. FIG. 5A shows that NIH 3T3 cells transfected with pZIPneo contain only inactive MAPK but that upon transformation with oncogenic H-Ras, MAPK is activated (FIG. 5A). Pretreatment with FTI-277 results in a concentration dependent inhibition of oncogenic Ras activation of MAPK. Concentrations as low as 300 nM were effective and the block was complete at 1 μM. Taken together, FIGS. 3 and 5 demonstrate that at least 50% inhibition of Ras processing is required for complete suppression of MAPK activation but that less than a 100% inhibition of Ras processing is required for complete suppression of MAPK activation by Ras. To determine whether the inhibition of MAPK activation is due to selectively antagonizing Ras function we have used a series of NIH 3T3 cell lines transformed with various oncogenes. Fig. 5B shows that FTI-277 was able to block H-RasF but not H-RasGG activation of MAPK and this is consistent with its ability to inhibit H-RasF but not H-RasGG processing (FIG. 2). Selectivity of FTI-277 towards antagonizing Ras-dependent activation of MAPK was substantiated by using NIH 3T3 cells where MAPK is constitutively activated by transformation with the Raf oncogene. FIG. 5B shows that oncogenic Raf activation of MAPK is not blocked by FTI-277 even though processing of endogenous Ras was inhibited in these cells. Similar results were also obtained with FTI-276 (FIG. 6). Taken together these results clearly demonstrate that FTI-276 and FTI-277 are highly effective and selective in disrupting contitutive Ras-specific activation of MAPK.

Thus, FTI-277 is an extremely potent and highly selective FTase inhibitor. This compound inhibited Ras processing with concentrations as low as 10 nM and processing was blocked at 1 $\mu$M. The most potent inhibitor previously reported BZA-5B, blocked Ras processing only at 150 $\mu$M (44). The tremendous increase in potency in intact cells is due to increased hydrophobicity of the central portion of the peptidomimetic. FTI-277 inhibition of FTase resulted in the accumulation of non-farnesylated, GTP-locked Ras in the cytoplasm where it was capable of binding Raf. This sequestration of Raf in the cytoplasm prevented its recruitment to the plasma membrane and subsequent activation. Thus, non-farnesylated, GTP locked Ras could act as a dominant inhibitor by sequestering its downstream effector. Support for this view is provided by results from FIGS. 2 and 5 which show that complete inhibition of MAPK activation was accomplished with FTI-277 concentrations which inhibited Ras processing only partially. FTI-277 was very selective in antagonizing Ras-specific signaling. The fact that FTI-277 suppressed only RasF but not RasGG or Raf oncogenic signaling demonstrates that the suppression is due to inhibition of Ras function and not the function of other farnesylated proteins that are required for Ras transformation.

EXAMPLE 20

ANTITUMOR EFFICACY AND SELECTIVITY OF FTI-276 AND FTI-277

In order to demonstrate the efficacy of these inhibitors as anticancer agents and show that they can inhibit tumor growth of human tumors which have multiple and complex genetic alterations, antitumor efficacy experiments were performed using a human tumor cell line. A critical issue connected with the potential use of the compounds of the invention is whether the growth of human tumors which harbor K-Ras mutations can be blocked. This is important for further development of FTase inhibitors as anticancer drugs since K-Ras mutations are most common in human cancers and since K-Ras processing is more difficult to inhibit than the processing of the less prevalent H-Ras (1–3, 15). Furthermore, the majority of human tumors have multiple genetic alternations; notably a delation in the tumor suppressor gene p53 is most prevalent. It is therefore extremely important to determine whether or not inhibition of Ras function is sufficient to halt the growth of human tumors which harbor K-Ras mutation as well as deletions in p53.

To evaluate the antitumor efficacy of FTI-276 we used a nude mouse xenograft model where human tumors are implanted subcutaneously and two human lung carcinoma cell lines. One of these (Calu-1) harbors a K-Ras oncogenic mutation and has a deletion of the tumor suppressor gene p53. The other human lung carcinoma (NCI-H180) has no Ras mutations. Thirty two days after s.c. implantation when the tumors reached sizes of 60 to 80 mm$^3$, the mice were randomly separated into control and treated groups (4 animals per group; each animal had a tumor on both the right and the left flank). FIG. 7A shows that tumors from control animals treated with saline once daily starting on day 36 grew to an average size of 566 mm$^3$ over a period of 64 days from tumor implantation. In contrast, tumors treated once daily with FTI-276 (50 mg/kg) grew very little and the average tumor size was 113 mm$^3$ (FIG. 7A). In another experiment, FTI-277, the methylester of FTI-276, inhibited the growth of Calu-I cells to the same extent (FIG. 8). Although the animals were treated once daily with 50 mg/kg for 36 days (total cumulative does of 1.8 g/kg), no weight loss was observed and the animals appeared normal with no evidence of gross toxicity. This lack of toxicity was also observed in separate experiments where the dose was escalated to 180 mg/kg once daily. Thus, FTI-276 and FTI-277 essentially blocked tumor growth of Calu-I carcinoma with no evidence of gross toxicity.

We also determined the effects of FTI-276 on the tumor growth of another human lung carcinoma, NCI-H810, that does not harbor an oncogenic Ras mutation. FIG. 7B shows that tumors from animals treated with saline or FTI-276 grew at a similar rate. Over a period of 14 days of treatment the average tumor size of the control and FTI-276 treated groups were 919 mm$^3$ and 815 mm$^3$, respectively. These results clearly demonstrate that in contrast to Calu-1, NCI-H810 carcinomas were not sensitive to FTI-276 treatment suggesting that FTI-276 inhibition of tumor growth of human lung carcinomas is Ras-dependent. Furthermore, FTI-276 inhibited tumor growth even though Calu-1 does not express p53. These surprising and significant results indicate that inhibition of oncogenic Ras function is sufficient to halt growth of human tumors with multiple genetic alternations.

To further establish the selectivity of FTI-276 to inhibit selectively Ras-dependent tumors, we determined the antitumor efficacy of FTI-276 and FTI-277 against H-RasF and Raf transformed NIH 3T3 in the same nude mouse xenograft model. FIG. 9 shows that a once daily injection of FTI-276 or FTI-277 (50 mg/kg) inhibited tumor growth of H-RasF transformed NIH 3T3 cells. In contrast, an identical treatment regimen with FTI-276 and FTI-277 had no effect on the growth of Raf-transformed NIH 3T3 cells (FIG. 10), further confirming the conclusion from the results of FIGS. 7 and 8 that FTI-276 and FTI-277 are selective for Ras-dependent tumors.

We also addressed the question of whether FTI-276 inhibition of tumor growth correlated with inhibition of Ras processing in vivo. To so this, mice having subcutaneous H-RasF cells were treated with various doses of FTI-276 (0, 10, 50 and 100 mg/kg) and tumor size and Ras processing in the HRasF tumors in vivo were examined. FIG. 11A shows that throughout the 11 day treatment period, FTI-276 inhibited tumor growth in a dose dependent fashion. The tumor sizes at the end of 17 days were 2490 mm$^3$ for saline, 1793 mm$^3$ for 10 mg/kg, 1226 mm$^3$ for 50 mg/kg and 624 mm$^3$ for 100 mg/kg treated animals. To determine the levels of inhibition of Ras processing, the animals were sacrificed 5 hrs after the last injection, the tumors were excised and processed for immunoblotting with anti-Ras antibody as described in legend to FIG. 11. Tumors from control animals contained only fully processed Ras which migrates faster in SDS-PAGE gels (FIG. 11B). As the dose of FTI-276 increases from 10 to 100 mg/kg there was a progressive accumulation of unprocessed Ras which was paralleled by a decrease in the relative ratio of fully processed Ras. Thus, the extent of tumor growth inhibition correlated with the extent of inhibition of Ras processing. Furthermore, the inhibition of Ras processing in vivo was selective in that FTI-276 did not inhibit Rap1A processing even at 100 mg/kg.

Literature references mentioned in the foregoing are more specifically identified as follows and are hereby incorporated herein by reference:

1. Barbacid, M., *Annu. Rev. Biochem.*, 56:779–828, (1987)
2. Grand, R. J. A. and Owen, D., *Biochem. J.*, 279:609–631, (1991)
3. Barbacid, M., *Important Advances in Oncology*, eds. Devita, Hellman & Rosenberg (Lippincott, Philadelphia, Pa), pp. 3–22, (1986)
4. Mulcahy, L. S., Smith, M. R., and Stacey, D. W., *Nature*, 313:241–243, (1985)
5. Noda, M., Ko, M., Ogura, A., Liu, D.G>, Amano, T., Takano, T. and Ikawa, Y., *Nature*, 318:73–75, (1985)
6. Bar-Sagi, D. and Feramisco, J. R., *Cell*, 42:841–848, (1985)
7. Kataoka, T., Powers, S., McGill, C., Fasano, O., Strathern, J., Broach, J. and Wigler, M., *Cell*, 37:437–445, (1984)
8. Willumsen, B. M., Christensen, A., Hubbert, N. C., Papageorge, A. G. and Lowy, D. R., *Nature*, 310:583–586, (1984)
9. Willumsen, B. M., Norris, K., Papageorge, A. G., Hubbert, N. C. and Lowy, D. R., *EMBO J.*, 3:2581–2585, (1984)
10. Hancock, J. F., Magee, A. I., Childs, J. E. and Marshall, C. J., *Cell*, 57:1167–1177, (1989)
11. Gutierrez, L., Magee, A. I., Marshall, C. J. and Hancock, J. F., *EMBO J*, 8:1093–1098, (1989)
12. Casey, P. J., Solski, P. A., Der, C. J. and Buss, J. E., *Proc. Natl. Acad. Sci. USA*, 86:8323–8327, (1989)
13. Jackson, J.H., Cochrane, C. G., Bourne, J. R., Solski, P. A., Buss, J. E. and Der, C. J., *Proc. Natl. Acad. Sci. USA*, 87:3042–3046, (1990)
14. Hancock, J. F., Paterson, H. and Marshall, J. C., Cell, 63:133–139, (1990)
15. Reiss, Y., Goldstein, J. L., Seabra, M. C., Casey, P. J. and Brown, M. S., *Cell*, 62:81–88, (1990)
16. Reiss, Y., Seabra, M. C., Goldstein, J. L. and Brown, M. S., *METHODS: A Companion to Methods in Enzymology*, 1:241–245, (1990)
17. Reiss, Y., Seabra, M. C., Armstrong, S.A., Slaughter, C. A., Goldstein, J. L. and Brown, M.S., J. Biol. Chem., 266:10672–10877, (1991)
18. Reiss, Y., Stradley, S. J., Gierasch, L. M., Brown, M. S. and Goldstein, J. L., *Proc. Natl. Acad. Sci. USA*, 88:732–736, (1991)
19. Manne, V., Roberts, D., Tobin, A., O'Rourke, E., DeVirgillio, M., Meyres, C., Ahmed, N., Kurz, E., Resh, M., Kung, H.F. and Barbacid, M., *Proc. Natl. Acad. Sci. USA*, 87:7541–7545, (1990)
20. Gibbs, J. B., *Cell*, 65:1–4, (1991)
21. Moores, S. L., Schaber,M. D., Mosser, S. D., Rands, E., O'Hara, M. B., Garsky, V. M., Marshall,M. S., Pompliano, D. L. and Gibbs, J. B., *J. Biol. Chem.*, 266:14603–14610, (1991)
22. Goldstein, J. L., Brown, M. S., Stradley, S. J., Reiss, Y. and Gierasch, L. M., *J. Biol. Chem.*, 266:15575–15578, (1991)
23. Brown, M. S., Goldstein, J. L., Paris, K. J., Burnier, J. P. and Marsters, J. C., *Proc. Natol. Acad. Sci. USA*, 89:8313–8316, (1992)
24. Pompliano, D. L., Rands, E., Schaber, M. D., Mosser, S.D., Neville, J. A. and Gibbs, J. B., Biochemistry, 31:3800–3807, (1992)
25. Lacal, J. D., Santos, E., Notario, V., Barbacid, M., Yamazaki, S., Kung, H. F., Seamans, O., McAndrew, S. and Crowl, R., *Proc. Natl. Acad. Sci. USA*, 81:5305–5309, (1984)
26. Stewart, F. H. C., Aus. J. Chem., 36:2511, (1983)
27. Brown, M. J., Milano, P. D., Lever, D. C., Epstein, W. W. and Poulter, C. D., *J. Am. Chem. Soc.*, 113:3176, (1991)
28. Yang, C. C., Marlowe, C. K. and Kania, R.,*J. Am. Chem. Soc.*, 113:3177, (1991)
29. McCormick, F. (1993) *Nature* 363:15–16.
30. McCormick, F. (1994) *Current Opinion in Genetics & Development* 4:71–76
31. Marshall, C. J. (1994) *Current Opinion in Genetics & Development* 4: 82–89
32. Kato, K., Cox, A. D., Hisaka, M. M., Graham, S. M., Buss, J. E., and Der, C. J. (1992) *Proc. Natl. Acad. Sci. USA* 89:6403–6407.
33. Gibbs, J. B., Oliff, A., and Kohl, N. E. (1994) Cell 77:175–178.
34. Nigam, M., Seong, C., Qian, Y., Hamilton, A. D., and Sebti, S. M. (1993) *J. Biol. Chem.* 268:20695–20698.
35. Qian, Y., Blaskovich, M. A., Saleem, M., Seong, C., Wathen, S. P., Hamilton, A. D., and Sebti, S. M. (1994) *J. Biol. Chem.* 269:12410–12413.
36. Qian, Y., Blaskovich, M. A., Seong, C. M., Vogt, A., Hamilton, A. D., and Sebti, S.M. (1994) *Bioorg. Med. Chem. Lett* 4:2579–2584.
37. Kohl, N. E., Mosser, S. D., deSolms, S. J., Giuliani, E. A., Pompliano, D. L., Graham, S. L., Smith, R. L., Scolnick, E. M., Oliff, A., and Gibbs, J. B. (1993) *Science* 260:1934–1937.
38. James, G. L., Goldstein, J. L., Brown, M. S., Rawson, T. E., Somers, T. C., McDowell, R. S., Crowley, C. W., Lucas, B. K., Levinson, A. D., and Marsters, J. C., Jr. (1993) *Science* 260:193–194.
39. Graham, S. L., deSolms, S. J., Giuliani, E. A., Kohl, N. E., Mosser, S. D., Oliff, A. I., Pompliano, D. L., Rands, E. Breslin, M. J., Deana, A. A., Garsky, V. M., Scholz, T. H., Gibbs, J. B., and Smith, R.L. (1994) *J. Med. Chem.* 37:725–732.
40. Garcia, A. M., Rowell, C. Ackerman, K., Kowalczyk, J. J., and Lewis, M. D. (1993) *J. Biol. Chem.* 268:18415–18418.
41. Vogt, A., Qian, Y., Blaskovich, M.A., Fossum, R. D., Hamilton, A. D., and Sebti, S. M. (1995) *J. Biol. Chem.* 270:660–664.
42. Kohl, N. E., Wilson, F. R., Mosser, S. D., Giuliani, E., deSolms, S. J., Conner, M. W., Anthony, N. J., Holtz, W. J., Gomez, R. P., Lee, T. J., and et al. (1994) *Proc. Natl. Acad. Sci. USA* 91:9141–9145.
43. Cox, A. D., Garcia, A. M., Westwick, J. K., Kowalczyk, J. J., Lewis, M. D., Brenner, D. A., and Der, C. J. (1994) J. Biol. Chem. 269:19203–19206.
44. James, G. L., Brown, M. S., Cobb, M. H., and Goldstein, J. L. (1994) *J. Biol. Chem.* 269:277705–277714.
45. Cox, A. D., Hisaka, M. M., Buss, J. E., and Der, C. J. (1992) *Mol. Cell. Biol.* 12:2606–2615.
46. Hallberg, B. Rayter, S. I., and Downward, J. (1994) *J. Biol. Chem.* 269:3913–3916.
47. Leevers, S. J., Paterson, H. F., and Marshall, C. J. (1994) Nature 369:411–414.

48. Stanton, V. P., Jr., Nichols, D. W., Laudano, A. P., Cooper, G. M. (1989) *Mol. Cell. Biol.* 9: 639–647.

It will be appreciated that various modifications may be made in the invention as described above without departing from the scope and intent of the invention as defined in the following claims wherein:

We claim:

1. A peptidonimetic of the formula:

CβX wherein

C is a cysteinyl moiety or a 3-mercapto-2-amino-propylamino group;

X is an amino acid; and

β is a residue of an aminobenzoic acid or an aminonaphthoic acid, which is optionally substituted with a substituent selected from the group consisting of alkyl, naphthyl, pyrrolyl, pyridyl, thiophenyl and phenyl, wherein the phenyl group is optionally substituted with one or more substituents selected from the group consisting of an alkoxy moiety, a chlorine atom, a bromine atom, and an alkyl moiety.

2. A peptidomimetic according to claim 1 wherein C, is a 3-mercapto-2-amino-propylamino group.

3. A peptidomimetic according to claim 2 wherein β is 2-pheyl-4-aminobenzoic acid.

4. A peptidomimetic according to claim 1 of the formula:

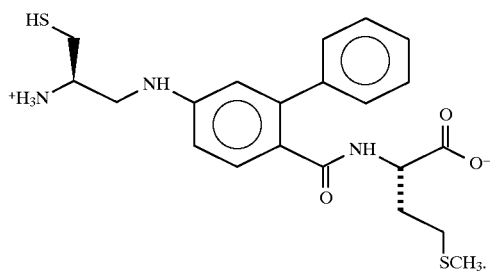

5. A peptidomimetic according to claim 1 wherein β is a substituted 4-aminobenzoic acid.

6. A peptidomimetic according to claim 1 wherein X is methionine or phenylalanine.

7. A pharmaceutical composition comprising a peptidomimetic according to one of claims 1–6 and a pharmaceutically acceptable carrier.

8. A compound of the formula:

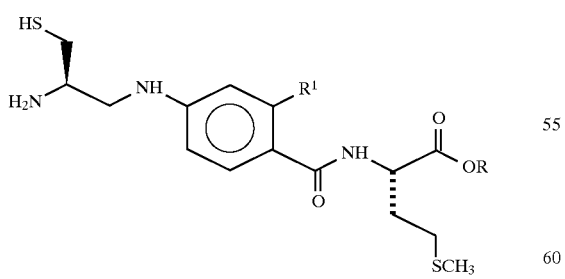

9. A compound according to claim 8 wherein $R^1$ is an unsubstituted phenyl group, or an alkoxy-, chloro-, bromo- or methyl- substituted phenyl group.

10. A compound according to claim 8 wherein $R^1$ is chosen from the group consisting ot a 3,5 dimethylphenyl radical, a thiophene radical, a naphthyl radical, a pyrrole radical, a pyridyl radical, an alkyl radical, and an alkoxy radical.

11. A compound of the formula

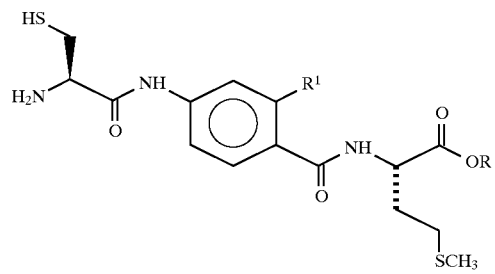

wherein R represents H or $CH_3$ ; or OR, taken together with the carbonyl group to which it is bonded, represents a lipophilic estrase-sensitive moiety, and $R^1$ represents a substiuent selected from the group consisting of hydrogen, alkyl, naphthyl, pyrrolyl, pyridyl, thiophenyl and phenyl, wherein the phenyl group is optionally substituted with one or more substituents selected from the group consisting of an alkoxy moiety, a chlorine atom, a bromine atom, and an alkyl moiety.

12. A compound according to claim 10 wherein $R^1$ is an unsubstituted phenyl group, or an alkoxy-, chloro-, bromo- or methyl- substituted phenyl group.

13. A compound according to claim 11 wherein $R^1$ is a 3,5 dimethylphenyl radical.

14. A compound of the formula

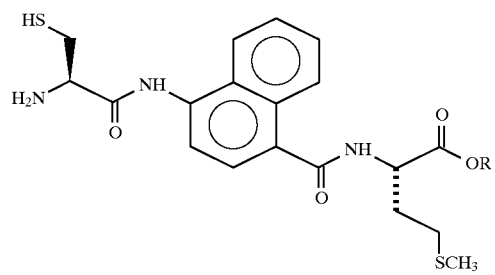

wherein R represents H, $CH_3$ or the substituent OR, taken together with the carbonyl group to which it is bonded, represents a lipophilic, esterase-sensitive moiety.

15. A compound of the formula

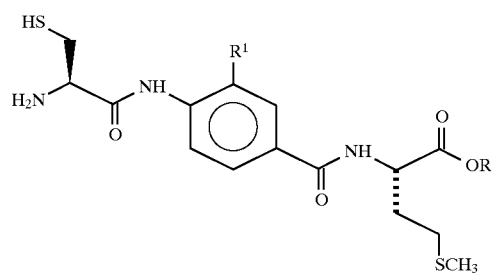

wherein R represents H, $CH_3$ or the substituent OR, taken together with the carbonyl group to which it is bonded, represents a lipophilic, esterase-sensitive moiety, and $R^1$ represents H, $CH_3$ or $OCH_3$.

16. A method of inhibiting farnesyltransferase in a host wherein farnesyltransferase is present comprising administering to said host an effective amount of a peptidomimetic according to any of claims 1–6 and 13–20.

17. A method of treating cancer comprising administering to a patient in need of such treatment an effective amount of a peptidomimetic according to one of claims 1–6 and 13–20.

* * * * *

UNITED STATES PATENT AND TRADEMARK OFFICE
CERTIFICATE OF CORRECTION

PATENT NO. : 5,834,434
DATED : November 10, 1998
INVENTOR(S) : Sebti et al

It is certified that error appears in the above-identified patent and that said Letters Patent is hereby corrected as shown below:

Please amend the claims as follows:

Claim 1, line 1, change "peptidonimetic" to --peptidomimetic--.

Claim 3, line 2, change "2-pheyl-4-aminobenzoic" to --2-phenyl-4-aminobenzoic--.

Claim 8, following the structural formula, insert

--wherein R represents H or $CH_3$; or OR, taken together with the carbonyl group to which it is bonded, represents a lipophilic esterase-sensitive moiety, and $R^1$ represents a substituent selected from the group consisting of hydrogen, alkyl, naphthyl, pyrrolyl, pyridyl, thiophenyl and phenyl, wherein the phenyl group is optionally substituted with one or more substituents selected from the group consisting of an alkoxy moiety, a chlorine atom, a bromine atom, and an alkyl moiety.--

Claim 11, line 5, change "estrase-sensitive" to --esterase-sensitive--;
line 6, change "substiuent" to --substituent--.

Signed and Sealed this

Twenty-eighth Day of March, 2000

Attest:

Q. TODD DICKINSON

Attesting Officer

Commissioner of Patents and Trademarks